US006379923B1

(12) United States Patent
Duan et al.

(10) Patent No.: US 6,379,923 B1
(45) Date of Patent: Apr. 30, 2002

(54) ELL2, A NEW MEMBER OF AN ELL FAMILY OF RNA POLYMERASE II ELONGATION FACTORS

(75) Inventors: D. Roxanne Duan, Bethesda, MD (US); Ali Shilatifard, St. Louis, MO (US); Joan W. Conaway; Ronald C. Conaway, both of Oklahoma City, OK (US)

(73) Assignees: Human Genome Sciences, Inc., Rockville, MD (US); Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/362,871

(22) Filed: Jul. 29, 1999

Related U.S. Application Data

(62) Division of application No. 09/026,343, filed on Feb. 19, 1998, now Pat. No. 6,008,018.

(60) Provisional application No. 60/038,447, filed on Feb. 19, 1997.

(51) Int. Cl.$^7$ ........................ C12N 15/63; C07K 14/435

(52) U.S. Cl. ........................ 435/69.1; 530/350

(58) Field of Search ........................ 530/350; 435/69.1

(56) References Cited

FOREIGN PATENT DOCUMENTS

WO WO 94/01548 1/1994

OTHER PUBLICATIONS

NCBI Entrez, GenBank Report, Accession No. AA655966, from Marra, M. et al. (Nov. 1997), with Revision History.
NCBI Entrez, GenBank Report, Accession No. AA743118, from NCI–CGAP (Jan. 1998), with Revision History.
NCBI Entrez, GenBank Report, Accession No. W13766, from Marra, M. et al. (Oct. 1997), with Revision History.
NCBI Entrez, GenBank Report, Accession No. AA252607, from NCI–CGAP (Aug. 1997), with Revision History.
NCBI Entrez, GenBank Report, Accession No. AA243384, from NCI–CGAP (Aug. 1997), with Revision History.
NCBI Entrez, GenBank Report, Accession No. AA524290, from NCI–CGAP (Aug. 1997), with Revision History.
NCBI Entrez, GenBank Report, Accession No. AA375277, from Adams, M.D. et al. (Apr. 1997), with Revision History.
NCBI Entrez, GenBank Report, Accession No. AA009921, from Hillier, L. et al. (May 1997), with Revision History.
NCBI Entrez, GenBank Report, Accession No. AA545429, from Marra, M. et al. (Aug. 1997), with Revision History.
NCBI Entrez, GenBank Report, Accession No. AA414990, from Marra, M. et al. (May 1997), with Revision History.
NCBI Entrez, GenBank Report, Accession No. AA370180, from Adams, M.D. et al. (Apr. 1997), with Revision History.
NCBI Entrez, GenBank Report, Accession No. AA370048, from Adams, M.D. et al. (Apr. 1997), with Revision History.
NCBI Entrez, GenBank Report, Accession No. W92650, from Hillier, L. et al. (Nov. 1996), with Revision History.
NCBI Entrez, GenBank Report, Accession No. W94585, from Hillier, L. et al. (Nov. 1996), with Revision History.
NCBI Entrez, GenBank Report, Accession No. AA191245, from Hillier, L. et al. (Jan. 1997), with Revision History.
NCBI Entrez, GenBank Report, Accession No. R12663, from Hillier, L. et al. (1995), with Revision History.
NCBI Entrez, GenBank Report, Accession No. R16400, from Hillier, L. et al. (1995), with Revision History.
NCBI Entrez, GenBank Report, Accession No. N39822, from Hillier, L. et al. (Jan. 1996), with Revision History.
Yu, H. et al., "Structural Basis for the Binding of Proline–Rich Peptides to SH3 Domains," *Cell 76*:933–945 (1994).
NCBI Entrez, GenBank Report, Accession No. Z20670, from MRC Human Genome Mapping Project Resource Centre (1995), with Revision History.
NCBI Entrez, GenBank Report, Accession No. T89063, from Hillier, L. et al. (1995), with Revision History.
Thirman, M.J. et al., "Cloning of ELL, a gene that fuses to MLL in a t(11;19)(q23;p13.1) in acute myeloid leukemia," *Proc. Natl. Acad. Sci. USA 91*:12110–12114 (1994).
Willott, E. et al., "The tight junction protein ZO–1 is homologous to the Drosophila discs–large tumor suppressor protein of a septate junctions," *Proc. Natl. Acad. Sci. USA 90*:7834–7838 (1993).
Woods, D.F. and P.J. Bryant, "The Discs–Large Tumor Suppressor Gene of Drosophila Encodes a Guanylate Kinase Homolog Localized at Septate Junctions," *Cell 66*:451–464 (1991).
Shilatifard, A. et al., "An RNA Polymerase II Elongation Factor Encoded by the Human ELL Gene," *Science 271*:1873–1876 (Mar. 1996).
Stark, M.J.R., "Multicopy expression vectors carrying the lac repressor gene for regulated high–level expression of genes in *Escherichia coli*," *Gene 51*:255–267 (1987).
Tan, S. et al., "A Bacteriophage Vector Suitable for Site–Directed Mutagenesis and High–Level Expression of Multisubunit Proteins in *E.coli*," *BioTechniques 16*:824–828 (1994).
Rice, G.A. et al., "Footprinting analysis of mammalian RNA polymerase II along its transcript: An alternative view of transcription elongation," *Proc. Natl. Acad. Sci. USA 88*:4245–4249 (1991).

(List continued on next page.)

*Primary Examiner*—John S. Brusca
(74) *Attorney, Agent, or Firm*—Sterne, Kessler, Goldstein & Fox P.L.L.C.

(57) ABSTRACT

ELL2 polypeptides and polynucleotides and methods for producing such polypeptides by recombinant techniques are disclosed. Also disclosed are methods for utilizing ELL2 polypeptides and polynucleotides in the design of protocols for the treatment of neoplastic disorders, among others and diagnostic assays for such conditions.

58 Claims, 7 Drawing Sheets

OTHER PUBLICATIONS

Ruff, P. et al., "Molecular identification of a major palmitoylated erythrocyte membrane protein containing the src homology 3 motif," *Proc. Natl. Acad. Sci. USA 88*:6595–6599 (1991).

Shilatifard, A. et al., "ELL2, a new member of an ELL family of RNA polymerase II elongation factors," *Proc. Natl. Acad. Sci. USA 94*:3639–3643 (Apr. 1997).

Price, D.H. et al., "Dynamic Interaction between a Drosophila Transcription Factor and RNA Polymerase II," *Mol. Cell. Biol. 9*:1465–1475 (1989).

Reines, D., "Nascent RNA Cleavage by Transcription Elongation Complexes," In: *Transcription: Mechanisms and Regulation*, Conaway, R.C. and J.W. Conaway, eds., Raven Press, Ltd., New York, NY, pp. 263–278 (1994).

Reines, D. et al., "The RNA polymerase II general elongation factors," *Trends in Biochemical Sci.* (*TiBS*) *21*:351–355 (Sep. 1996).

Marshall, N.F. and D.H. Price, "Purification of P–TEFb, a Transcription Factor Required for the Transition into Productive Elongation," *J. Biol. Chem. 270*:12335–12338 (1995).

Marshall, N.F. et al., "Control of RNA Polymerase II Elongation Potential by a Novel Carboxyl–terminal Domain Kinase," *J. Biol. Chem. 271*:27176–27183 (Oct. 1996).

Mitani, K. et al., "Cloning of Several Species of MLL/MEN Chimeric cDNAs in Myeloid Leukemia With t(11;19)(q23;p13.1) Translocation," *Blood 85*:2017–2024 (1995).

Kunkel, T.A., "Rapid and efficient site–specific mutagenesis without phenotypic selection," *Proc. Natl. Acad. Sci. USA 82*:488–492 (1985).

Lee, S. et al., "Nuclear/cytoplasmic localization of the von Hippel–Lindau tumor suppressor gene product is determined by cell density," *Proc. Natl. Acad. Sci. USA 93*:1770–1775 (Mar. 1996).

Lue, R.A. et al., "Cloning and characterization of hdlg: The human homologue of the Drosophila discs large tumor suppressor binds to protein 4.1," *Proc. Natl. Acad. Sci. USA 91*:9818–9822 (1994).

Jones, K.A. and B.M. Peterlin, "Control of RNA Initiation and Elongation at the HIV–1 Promoter," *Annu. Rev. Biochem. 63*:717–743 (1994).

Kibel, A. et al., "Binding of the von Hippel–Lindau Tumor Suppressor Protein to Elongin B and C," *Science 269*:1444–1446 (1995).

Kistner, U. et al., "SAP90, a Rat Presynaptic Protein Related to the Product of the Drosophila Tumor Suppressor Gene dlg–A," *J. Biol. Chem. 268*:4580–4583 (1993).

Furuse, M. et al., "Occludin: A Novel Integral Membrane Protein Localizing at Tight Junctions," *J. Cell Biol. 123*(*6*):1777–1788 (1993).

Gribskov, M. and R.R. Burgess, "Sigma Factors from *E. coli, B. subtilis*, phage SP01, and phage T4 are homologous proteins," *Nucl. Acids Res. 14*:6745–6763 (1986).

Jesaitis, L.A. and D.A. Goodenough, "Molecular Characterization and Tissue Distribution of ZO–2, A Tight Junction Protein Homologous to ZO–1 and the Drosophila Discs–Large Tumor Suppressor Protein," *J. Cell Biol. 124*:949–961 (1994).

Bentley, D.L., "Regulation of transcriptional elongation by RNA polymerase II," *Curr. Opin. Genetics & Develop. 5*:210–216 (1995).

Duan, D.R. et al., "Inhibition of Transcription Elongation by the VHL Tumor Suppressor Protein," *Science 269*:1402–1406 (1995).

Furuse, M. et al., "Direct Association of Occludin with ZO–1 and Its Possible Involvement in the Localization of Occludin at Tight Junctions," *J. Cell Biol. 127*:1617–1626 (1994).

Amann, E. et al., "Tightly regulated tac promoter vectors useful for the expression of unfused and fused proteins in *Escherichia coli*," *Gene 69*:301–315 (1988).

Aso, T. et al., "Elongin (SIII): A Multisubunit Regulator of Elongation by RNA Polymerase II," *Science 269*:1439–1443 (1995).

Aso, T. et al., "Transcription Syndromes and the Role of RNA Polymerase II General Transcription Factors in Human Disease," *J. Clin. Invest. 97*:1561–1569 (Apr. 1996).

Adams, M.D. et al., "Complementary DNA Sequencing: Expressed Sequence Tags and Human Genome Project," *Science 252*:1651–1656 (1991).

Adams, M.D. et al., "Sequence identification of 2,375 human brain genes," *Nature 355*:632–634 (1992).

Adams, M.D. et al., "Initial assessment of human gene diversity and expression patterns based upon 83 million nucleotides of cDNA sequence," *Nature 377*:3–174 (1995).

```
    CAGTGGCGGCGGGTGCAGAAGCCCAAGCAGCGCGGCCGCAGTGGAGGCTAGAGCCGGAGC
1   ---------+---------+---------+---------+---------+---------+   60

    GGCGGCGGCGGCGGCACCCCGGGGAGGTTTAAGATGGCGGCGGGGGGGACAGGGGGCCTG
61  ---------+---------+---------+---------+---------+---------+   120
                                     M  A  A  G  G  T  G  G  L

    CGGGAGGAGCAGCGCTATGGGCTGTCGTGCGGACGGCTGGGGCAGGACAACATCACCGTA
121 ---------+---------+---------+---------+---------+---------+   180
    R  E  E  Q  R  Y  G  L  S  C  G  R  L  G  Q  D  N  I  T  V

    CTGCATGTGAAGCTCACCGAGACGGCGATCCGGGCGCTCGAGACTTACCAGAGCCACAAG
181 ---------+---------+---------+---------+---------+---------+   240
    L  H  V  K  L  T  E  T  A  I  R  A  L  E  T  Y  Q  S  H  K

    AATTTAATTCCTTTTCGACCTTCAATCCAGTTCCAAGGACTCCACGGGCTTGTCAAAATT
241 ---------+---------+---------+---------+---------+---------+   300
    N  L  I  P  F  R  P  S  I  Q  F  Q  G  L  H  G  L  V  K  I

    CCCAAAAATGATCCCCTCAATGAAGTTCATAACTTTAACTTTTATTTGTCAAATGTGGGC
301 ---------+---------+---------+---------+---------+---------+   360
    P  K  N  D  P  L  N  E  V  H  N  F  N  F  Y  L  S  N  V  G

    AAAGACAACCCTCAGGGCAGCTTTGACTGCATCCAGCAAACATTCTCCAGCTCTGGAGCC
361 ---------+---------+---------+---------+---------+---------+   420
    K  D  N  P  Q  G  S  F  D  C  I  Q  Q  T  F  S  S  S  G  A

    TCCCAGCTCAATTGCCTGGGATTTATACAAGATAAAATTACAGTGTGTGCAACAAACGAC
421 ---------+---------+---------+---------+---------+---------+   480
    S  Q  L  N  C  L  G  F  I  Q  D  K  I  T  V  C  A  T  N  D

    TCGTATCAGATGACACGAGAAAGAATGACCCAGGCAGAGGAGGAATCCCGCAACCGAAGC
481 ---------+---------+---------+---------+---------+---------+   540
    S  Y  Q  M  T  R  E  R  M  T  Q  A  E  E  E  S  R  N  R  S

    ACAAAAGTTATCAAACCCGGTGGACCATATGTAGGGAAAAGAGTGCAAATTCGGAAAGCA
541 ---------+---------+---------+---------+---------+---------+   600
    T  K  V  I  K  P  G  G  P  Y  V  G  K  R  V  Q  I  R  K  A

    CCTCAAGCTGTTTCAGATACAGTTCCTGAGAGGAAAAGGTCAACCCCCATGAACCCTGCA
601 ---------+---------+---------+---------+---------+---------+   660
    P  Q  A  V  S  D  T  V  P  E  R  K  R  S  T  P  M  N  P  A

    AATACAATTCGAAAGACACATAGCAGCAGCACCATCTCTCAGAGGCCATACAGGGACAGG
661 ---------+---------+---------+---------+---------+---------+   720
    N  T  I  R  K  T  H  S  S  S  T  I  S  Q  R  P  Y  R  D  R

    GTGATTCACTTACTGGCCCTGAAGGCCTACAAGAAACCGGAGCTACTTGCTAGACTCCAG
721 ---------+---------+---------+---------+---------+---------+   780
    V  I  H  L  L  A  L  K  A  Y  K  K  P  E  L  L  A  R  L  Q
```

FIG.1A

```
     AAAGATGGTGTCAATCAAAAAGACAAGAACTCCCTGGGAGCAATTCTGCAACAGGTAGCC
 781 ---------+---------+---------+---------+---------+---------+  840
     K  D  G  V  N  Q  K  D  K  N  S  L  G  A  I  L  Q  Q  V  A

     AATCTGAATTCTAAGGACCTCTCATATACCTTAAAGGATTATGTTTTTAAAGAGCTTCAA
 841 ---------+---------+---------+---------+---------+---------+  900
     N  L  N  S  K  D  L  S  Y  T  L  K  D  Y  V  F  K  E  L  Q

     AGAGACTGGCCTGGATACAGTGAAATAGACAGACGGTCATTGGAGTCAGTGCTCTCTAGA
 901 ---------+---------+---------+---------+---------+---------+  960
     R  D  W  P  G  Y  S  E  I  D  R  R  S  L  E  S  V  L  S  R

     AAACTAAATCCGTCTCAGAATGCTACAGGCACCAGCCGTTCAGAATCTCCTGTATGTTCT
 961 ---------+---------+---------+---------+---------+---------+  1020
     K  L  N  P  S  Q  N  A  T  G  T  S  R  S  E  S  P  V  C  S

     AGTAGAGATGCTGTATCTTCTCCTCAGAAACGGCTTTTGGATTCAGAGTTTATTGATCCT
1021 ---------+---------+---------+---------+---------+---------+  1080
     S  R  D  A  V  S  S  P  Q  K  R  L  L  D  S  E  F  I  D  P

     TTAATGAATAAAAAAGCCCGAATATCTCACCTGACGAACAGAGTACCACCAACACTAAAT
1081 ---------+---------+---------+---------+---------+---------+  1140
     L  M  N  K  K  A  R  I  S  H  L  T  N  R  V  P  P  T  L  N

     GGTCATTTGAATCCCACCAGTGAAAAATCGGCTGCAGGCCTCCCACTGCCCCCTGCGGCT
1141 ---------+---------+---------+---------+---------+---------+  1200
     G  H  L  N  P  T  S  E  K  S  A  A  G  L  P  L  P  P  A  A

     GCTGCCATCCCCACCCCTCCACCGCTGCCTTCAACCTATCTGCCCATCTCACATCCTCCT
1201 ---------+---------+---------+---------+---------+---------+  1260
     A  A  I  P  T  P  P  P  L  P  S  T  Y  L  P  I  S  H  P  P

     CAGATTGTAAATTCTAACTCCAACTCCCCTAGCACTCCAGAAGGCCGGGGGACTCAAGAC
1261 ---------+---------+---------+---------+---------+---------+  1320
     Q  I  V  N  S  N  S  N  S  P  S  T  P  E  G  R  G  T  Q  D

     CTACCTGTTGACAGTTTTAGTCAAAACGATAGTATCTATGAGGACCAGCAAGACAAATAT
1321 ---------+---------+---------+---------+---------+---------+  1380
     L  P  V  D  S  F  S  Q  N  D  S  I  Y  E  D  Q  Q  D  K  Y

     ACCTCTAGGACTTCTCTGGAAACCTTACCCCCTGGTTCCGTTCTACTAAAGTGTCCAAAG
1381 ---------+---------+---------+---------+---------+---------+  1440
     T  S  R  T  S  L  E  T  L  P  P  G  S  V  L  L  K  C  P  K

     CCTATGGAAGAAAACCATTCAATGTCTCACAAAAAGTCCAAAAAGAAGTCTAAAAAACAT
1441 ---------+---------+---------+---------+---------+---------+  1500
     P  M  E  E  N  H  S  M  S  H  K  K  S  K  K  K  S  K  K  H

     AAGGAAAAGGACCAAATAAAAAAGCACGACATTGAGACTATTGAGGAAAAGGAGGAAGAT
1501 ---------+---------+---------+---------+---------+---------+  1560
     K  E  K  D  Q  I  K  K  H  D  I  E  T  I  E  E  K  E  E  D

     CTTAAGAGAGAAGAGGAAATTGCCAAGCTAAATAACTCCAGTCCAAATTCCAGTGGAGGA
1561 ---------+---------+---------+---------+---------+---------+  1620
```

```
     L  K  R  E  E  E  I  A  K  L  N  N  S  S  P  N  S  S  G  G

     GTTAAAGAGGATTGCACTGCCTCCATGGAACCTTCAGCAATTGAACTCCCAGATTATTTG
1621 ---------+---------+---------+---------+---------+---------+ 1680
     V  K  E  D  C  T  A  S  M  E  P  S  A  I  E  L  P  D  Y  L

     ATAAAATATATCGCTATCGTCTCCTATGAGCAACGCCAGAATTATAAGGATGACTTCAAT
1681 ---------+---------+---------+---------+---------+---------+ 1740
     I  K  Y  I  A  I  V  S  Y  E  Q  R  Q  N  Y  K  D  D  F  N

     GCAGAGTATGATGAGTACAGAGCTTTGCATGCCAGGATGGAGACTGTAGCTAGAAGATTT
1741 ---------+---------+---------+---------+---------+---------+ 1800
     A  E  Y  D  E  Y  R  A  L  H  A  R  M  E  T  V  A  R  R  F

     ATCAAACTAGATGCACAAAGAAAGCGCCTTTCTCCAGGCTCAAAAGAGTATCAGAATGTT
1801 ---------+---------+---------+---------+---------+---------+ 1860
     I  K  L  D  A  Q  R  K  R  L  S  P  G  S  K  E  Y  Q  N  V

     CATGAAGAAGTCTTACAAGAATATCAGAAGATAAAGCAGTCTAGTCCCAATTACCATGAA
1861 ---------+---------+---------+---------+---------+---------+ 1920
     H  E  E  V  L  Q  E  Y  Q  K  I  K  Q  S  S  P  N  Y  H  E

     GAAAAATACAGATGTGAATATCTTCATAACAAGCTGGCTCACATCAAAAGGCTAATAGGT
1921 ---------+---------+---------+---------+---------+---------+ 1980
     E  K  Y  R  C  E  Y  L  H  N  K  L  A  H  I  K  R  L  I  G

     GAATTTGACCAACAGCAAGCAGAGTCATGGTCCTAGAACTCTGCTTGGACCAGAAGATGT
1981 ---------+---------+---------+---------+---------+---------+ 2040
     E  F  D  Q  Q  Q  A  E  S  W  S  *

     GAATAAACTTAAGCTTATTTATTTAAAATTCCAAATGAGTTGCTCTAGATTCTAAAAAGG
2041 ---------+---------+---------+---------+---------+---------+ 2100

     TGAAACTTTGGCTGTTGAAAGTTTCAGTATTAGTAAACT
2101 ---------+---------+---------+---------   2139
```

FIG. 1C

```
ELL2  maaggtGGLREEQRYGLSCGRLgqd-NITVLHVKLTETAIRALETTYQSHKNLIPFRPSIQFQGLHGLVKIPKNDPLNEVH   79
ELL   m-----AALKEDRSYGLSGGRVSdgskVSVFHVKLIDSAIRAFESYRARQDSVSLRPSIRFQGSGQHISIPQPDCPAEAR     75

ELL2  NFNFYLSNVGKDNPQGSFDCIIQQTFSSSGASQLNCLGFIQDKITVCATNDSYQMTRERMTQAEEESRNRSTKVIKPGGPY   159
ELL   TFSFYLSNIGRDNPQGSFDCIIQQYVSSHGEVHLDCLGSIQDKITVCATDDSYQKARQSMAQAEEEIIRSRSAIVIKAGGRY  155

ELL2  VGKRVQIRKAPQAVSDTIVPERKRSTIPMNPANTIRKTHSS-----STTISQRPYRDRVIHLLALKAYKKPELLIARLQKDGVN  234
ELL   LGKKVQFRKPAPGATIDAVPSRKRATPINLASAIRKSGASQvsggSGVSQRPYRDRVIHLLALRPYRKAELLLRLQKDGLT    235

ELL2  QKDKNSLGAILQQVANLNSKDLSYTLKDYVFKELQRDWPGYSEIDRRSLESVLSRKLnpsqnat---GTSRSESPVCSSR     311
ELL   QADKDALDGILQQVANMSAKDGTICLTLQDCMYKDVQKDWPGYSEGDQQLLKRVLVRKLcqpqstgslIGDPAASSPPGERG   315

ELL2  DAVSSPQKRLLDSEFTIDPLMNKKARISHLTNRVPPITLNGHLnptseeksdaqiplppaaaiptpppIpstylpishppqi   391
ELL   RSASPPQKRLQPPLFIIDPLANKKPRISHFTQRAQPAVNGKLgvpngrealIptpgppastdtIsssthlpprtepprahd   395

ELL2  vnsnsnspstpegrgtqolpvdsfsqndsiyedqqdkytsrtsletlppgsVLLKCPKPMEENHSMHKKSKKKSKKHKE      471
ELL   pladvsndlghsgrdcehgeaqapaptvrIglp-----------------LLTDCAQPSRPHGSPSRSKPKKKSKKHKD     457

ELL2  KDQikKhdietieekeedlkreeeiqkIfnssspnssggvkedcTASMEPSAIELPDYLIKMIATVSYEQRQNYKDDFNAE    551
ELL   KERaaedkpraqIpdcapathatpgapadtpglngtcs-----VSSVPTSTSEITPDYLLKYAAISSSEQRQSYKNDFNAE   532

ELL2  YDEYRALHARMETVARRFIKLDAQRKRLSPGSKEYQNVHEEVLQEYQKIKQSSPNYHEEKYRCEYLIHKLAHIKRLIGEF     631
ELL   YSEYRDLHARIERITRRFITQLDAQLRQLSQGSEEYETTRGQILQEYRKIKKTNTNYSQEKHRCEYLIHSKLAHIKRLIAEY   612

ELL2  DQQQAESWs                                                                           640
ELL   DQRQLQAWp                                                                           621
```

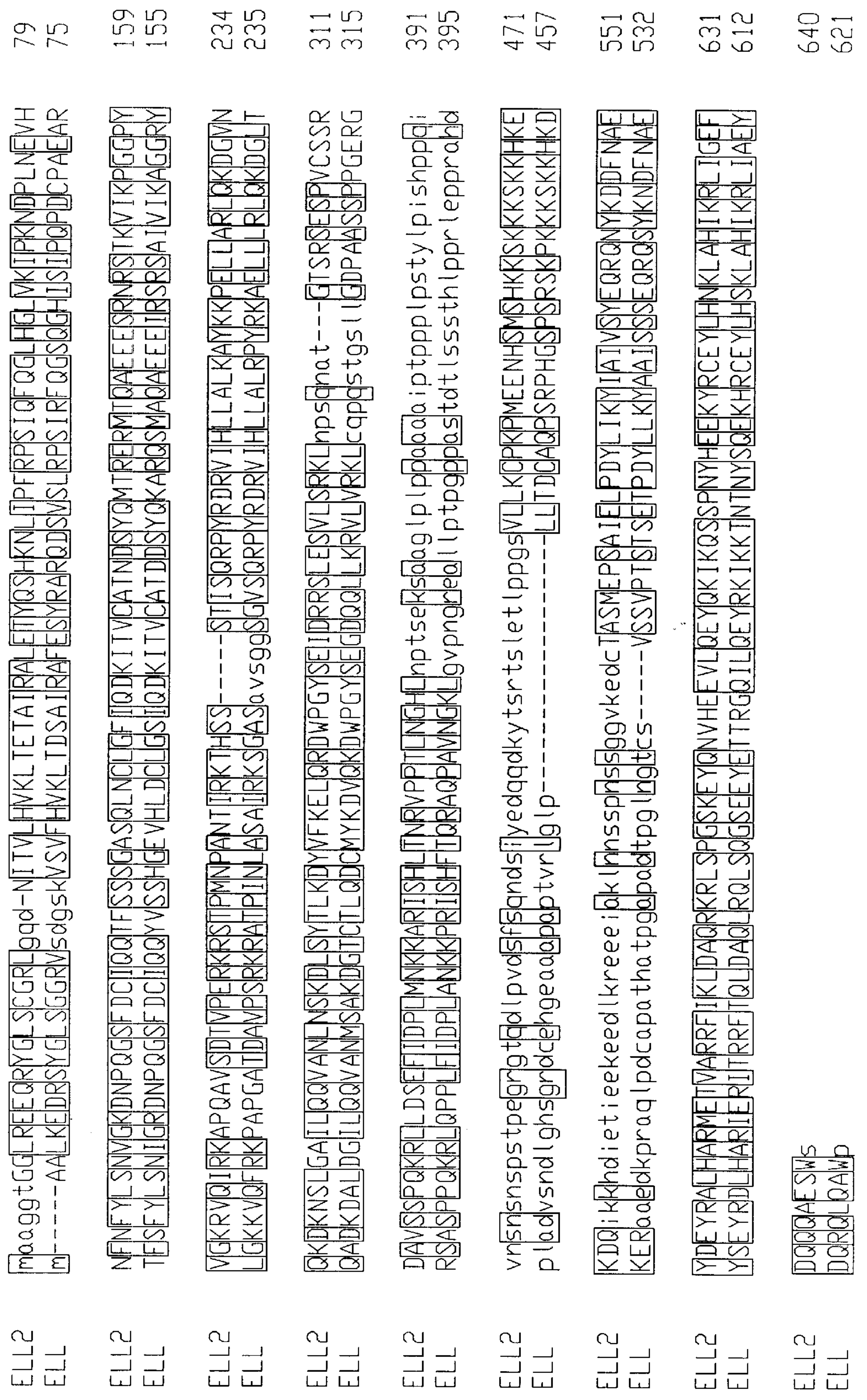

FIG. 2

```
                         SEQUENCE LISTING


(1) GENERAL INFORMATION:

   (iii) NUMBER OF SEQUENCES: 34


(2) INFORMATION FOR SEQ ID NO:1:

     (i) SEQUENCE CHARACTERISTICS:
          (A) LENGTH: 2139 base pairs
          (B) TYPE: nucleic acid
          (C) STRANDEDNESS: double
          (D) TOPOLOGY: both

    (ii) MOLECULE TYPE: cDNA

    (ix) FEATURE:
          (A) NAME/KEY: CDS
          (B) LOCATION: 94..2013

    (xi) SEQUENCE DESCRIPTION: SEQ ID NO:1:

CAGTGGCGGC GGGTGCAGAA GCCCAAGCAG CGCGGCCGCA GTGGAGGCTA GAGCCGGAGC      60

GGCGGCGGCG GCGGCACCCC GGGGAGGTTT AAG ATG GCG GCG GGG GGG ACA GGG      114
                                     Met Ala Ala Gly Gly Thr Gly
                                      1               5

GGC CTG CGG GAG GAG CAG CGC TAT GGG CTG TCG TGC GGA CGG CTG GGG      162
Gly Leu Arg Glu Glu Gln Arg Tyr Gly Leu Ser Cys Gly Arg Leu Gly
         10                  15                  20

CAG GAC AAC ATC ACC GTA CTG CAT GTG AAG CTC ACC GAG ACG GCG ATC      210
Gln Asp Asn Ile Thr Val Leu His Val Lys Leu Thr Glu Thr Ala Ile
     25                  30                  35

CGG GCG CTC GAG ACT TAC CAG AGC CAC AAG AAT TTA ATT CCT TTT CGA      258
Arg Ala Leu Glu Thr Tyr Gln Ser His Lys Asn Leu Ile Pro Phe Arg
 40                  45                  50                  55

CCT TCA ATC CAG TTC CAA GGA CTC CAC GGG CTT GTC AAA ATT CCC AAA      306
Pro Ser Ile Gln Phe Gln Gly Leu His Gly Leu Val Lys Ile Pro Lys
                 60                  65                  70
```

-continued

```
AAT GAT CCC CTC AAT GAA GTT CAT AAC TTT AAC TTT TAT TTG TCA AAT       354
Asn Asp Pro Leu Asn Glu Val His Asn Phe Asn Phe Tyr Leu Ser Asn
             75                  80                  85

GTG GGC AAA GAC AAC CCT CAG GGC AGC TTT GAC TGC ATC CAG CAA ACA       402
Val Gly Lys Asp Asn Pro Gln Gly Ser Phe Asp Cys Ile Gln Gln Thr
         90                  95                 100

TTC TCC AGC TCT GGA GCC TCC CAG CTC AAT TGC CTG GGA TTT ATA CAA       450
Phe Ser Ser Ser Gly Ala Ser Gln Leu Asn Cys Leu Gly Phe Ile Gln
    105                 110                 115

GAT AAA ATT ACA GTG TGT GCA ACA AAC GAC TCG TAT CAG ATG ACA CGA       498
Asp Lys Ile Thr Val Cys Ala Thr Asn Asp Ser Tyr Gln Met Thr Arg
120                 125                 130                 135

GAA AGA ATG ACC CAG GCA GAG GAG GAA TCC CGC AAC CGA AGC ACA AAA       546
Glu Arg Met Thr Gln Ala Glu Glu Glu Ser Arg Asn Arg Ser Thr Lys
                140                 145                 150

GTT ATC AAA CCC GGT GGA CCA TAT GTA GGG AAA AGA GTG CAA ATT CGG       594
Val Ile Lys Pro Gly Gly Pro Tyr Val Gly Lys Arg Val Gln Ile Arg
            155                 160                 165

AAA GCA CCT CAA GCT GTT TCA GAT ACA GTT CCT GAG AGG AAA AGG TCA       642
Lys Ala Pro Gln Ala Val Ser Asp Thr Val Pro Glu Arg Lys Arg Ser
        170                 175                 180

ACC CCC ATG AAC CCT GCA AAT ACA ATT CGA AAG ACA CAT AGC AGC AGC       690
Thr Pro Met Asn Pro Ala Asn Thr Ile Arg Lys Thr His Ser Ser Ser
    185                 190                 195

ACC ATC TCT CAG AGG CCA TAC AGG GAC AGG GTG ATT CAC TTA CTG GCC       738
Thr Ile Ser Gln Arg Pro Tyr Arg Asp Arg Val Ile His Leu Leu Ala
200                 205                 210                 215

CTG AAG GCC TAC AAG AAA CCG GAG CTA CTT GCT AGA CTC CAG AAA GAT       786
Leu Lys Ala Tyr Lys Lys Pro Glu Leu Leu Ala Arg Leu Gln Lys Asp
                220                 225                 230

GGT GTC AAT CAA AAA GAC AAG AAC TCC CTG GGA GCA ATT CTG CAA CAG       834
Gly Val Asn Gln Lys Asp Lys Asn Ser Leu Gly Ala Ile Leu Gln Gln
            235                 240                 245

GTA GCC AAT CTG AAT TCT AAG GAC CTC TCA TAT ACC TTA AAG GAT TAT       882
Val Ala Asn Leu Asn Ser Lys Asp Leu Ser Tyr Thr Leu Lys Asp Tyr
        250                 255                 260

GTT TTT AAA GAG CTT CAA AGA GAC TGG CCT GGA TAC AGT GAA ATA GAC       930
Val Phe Lys Glu Leu Gln Arg Asp Trp Pro Gly Tyr Ser Glu Ile Asp
    265                 270                 275

AGA CGG TCA TTG GAG TCA GTG CTC TCT AGA AAA CTA AAT CCG TCT CAG       978
Arg Arg Ser Leu Glu Ser Val Leu Ser Arg Lys Leu Asn Pro Ser Gln
280                 285                 290                 295

AAT GCT ACA GGC ACC AGC CGT TCA GAA TCT CCT GTA TGT TCT AGT AGA      1026
Asn Ala Thr Gly Thr Ser Arg Ser Glu Ser Pro Val Cys Ser Ser Arg
                300                 305                 310

GAT GCT GTA TCT TCT CCT CAG AAA CGG CTT TTG GAT TCA GAG TTT ATT      1074
Asp Ala Val Ser Ser Pro Gln Lys Arg Leu Leu Asp Ser Glu Phe Ile
            315                 320                 325

GAT CCT TTA ATG AAT AAA AAA GCC CGA ATA TCT CAC CTG ACG AAC AGA      1122
Asp Pro Leu Met Asn Lys Lys Ala Arg Ile Ser His Leu Thr Asn Arg
        330                 335                 340

GTA CCA CCA ACA CTA AAT GGT CAT TTG AAT CCC ACC AGT GAA AAA TCG      1170
Val Pro Pro Thr Leu Asn Gly His Leu Asn Pro Thr Ser Glu Lys Ser
    345                 350                 355

GCT GCA GGC CTC CCA CTG CCC CCT GCG GCT GCT GCC ATC CCC ACC CCT      1218
Ala Ala Gly Leu Pro Leu Pro Pro Ala Ala Ala Ala Ile Pro Thr Pro
360                 365                 370                 375

CCA CCG CTG CCT TCA ACC TAT CTG CCC ATC TCA CAT CCT CCT CAG ATT      1266
Pro Pro Leu Pro Ser Thr Tyr Leu Pro Ile Ser His Pro Pro Gln Ile
                380                 385                 390
```

-continued

```
GTA AAT TCT AAC TCC AAC TCC CCT AGC ACT CCA GAA GGC CGG GGG ACT     1314
Val Asn Ser Asn Ser Asn Ser Pro Ser Thr Pro Glu Gly Arg Gly Thr
            395                 400                 405

CAA GAC CTA CCT GTT GAC AGT TTT AGT CAA AAC GAT AGT ATC TAT GAG     1362
Gln Asp Leu Pro Val Asp Ser Phe Ser Gln Asn Asp Ser Ile Tyr Glu
        410                 415                 420

GAC CAG CAA GAC AAA TAT ACC TCT AGG ACT TCT CTG GAA ACC TTA CCC     1410
Asp Gln Gln Asp Lys Tyr Thr Ser Arg Thr Ser Leu Glu Thr Leu Pro
    425                 430                 435

CCT GGT TCC GTT CTA CTA AAG TGT CCA AAG CCT ATG GAA GAA AAC CAT     1458
Pro Gly Ser Val Leu Leu Lys Cys Pro Lys Pro Met Glu Glu Asn His
440                 445                 450                 455

TCA ATG TCT CAC AAA AAG TCC AAA AAG AAG TCT AAA AAA CAT AAG GAA     1506
Ser Met Ser His Lys Lys Ser Lys Lys Lys Ser Lys Lys His Lys Glu
                460                 465                 470

AAG GAC CAA ATA AAA AAG CAC GAC ATT GAG ACT ATT GAG GAA AAG GAG     1554
Lys Asp Gln Ile Lys Lys His Asp Ile Glu Thr Ile Glu Glu Lys Glu
            475                 480                 485

GAA GAT CTT AAG AGA GAA GAG GAA ATT GCC AAG CTA AAT AAC TCC AGT     1602
Glu Asp Leu Lys Arg Glu Glu Glu Ile Ala Lys Leu Asn Asn Ser Ser
        490                 495                 500

CCA AAT TCC AGT GGA GGA GTT AAA GAG GAT TGC ACT GCC TCC ATG GAA     1650
Pro Asn Ser Ser Gly Gly Val Lys Glu Asp Cys Thr Ala Ser Met Glu
    505                 510                 515

CCT TCA GCA ATT GAA CTC CCA GAT TAT TTG ATA AAA TAT ATC GCT ATC     1698
Pro Ser Ala Ile Glu Leu Pro Asp Tyr Leu Ile Lys Tyr Ile Ala Ile
520                 525                 530                 535

GTC TCC TAT GAG CAA CGC CAG AAT TAT AAG GAT GAC TTC AAT GCA GAG     1746
Val Ser Tyr Glu Gln Arg Gln Asn Tyr Lys Asp Asp Phe Asn Ala Glu
                540                 545                 550

TAT GAT GAG TAC AGA GCT TTG CAT GCC AGG ATG GAG ACT GTA GCT AGA     1794
Tyr Asp Glu Tyr Arg Ala Leu His Ala Arg Met Glu Thr Val Ala Arg
            555                 560                 565

AGA TTT ATC AAA CTA GAT GCA CAA AGA AAG CGC CTT TCT CCA GGC TCA     1842
Arg Phe Ile Lys Leu Asp Ala Gln Arg Lys Arg Leu Ser Pro Gly Ser
        570                 575                 580

AAA GAG TAT CAG AAT GTT CAT GAA GAA GTC TTA CAA GAA TAT CAG AAG     1890
Lys Glu Tyr Gln Asn Val His Glu Glu Val Leu Gln Glu Tyr Gln Lys
    585                 590                 595

ATA AAG CAG TCT AGT CCC AAT TAC CAT GAA GAA AAA TAC AGA TGT GAA     1938
Ile Lys Gln Ser Ser Pro Asn Tyr His Glu Glu Lys Tyr Arg Cys Glu
600                 605                 610                 615

TAT CTT CAT AAC AAG CTG GCT CAC ATC AAA AGG CTA ATA GGT GAA TTT     1986
Tyr Leu His Asn Lys Leu Ala His Ile Lys Arg Leu Ile Gly Glu Phe
                620                 625                 630

GAC CAA CAG CAA GCA GAG TCA TGG TCC TAGAACTCTG CTTGGACCAG           2033
Asp Gln Gln Gln Ala Glu Ser Trp Ser
            635                 640

AAGATGTGAA TAAACTTAAG CTTATTTATT TAAAATTCCA AATGAGTTGC TCTAGATTCT   2093

AAAAAGGTGA AACTTTGGCT GTTGAAAGTT TCAGTATTAG TAAACT                  2139
```

(2) INFORMATION FOR SEQ ID NO:2:

(i) SEQUENCE CHARACTERISTICS:
(A) LENGTH: 640 amino acids
(B) TYPE: amino acid
(D) TOPOLOGY: linear (ii) MOLECULE TYPE: protein -continued (xi) SEQUENCE DESCRIPTION: SEQ ID NO:2:

```
Met Ala Ala Gly Gly Thr Gly Gly Leu Arg Glu Glu Gln Arg Tyr Gly
  1               5                  10                  15

Leu Ser Cys Gly Arg Leu Gly Gln Asp Asn Ile Thr Val Leu His Val
             20                  25                  30

Lys Leu Thr Glu Thr Ala Ile Arg Ala Leu Glu Thr Tyr Gln Ser His
         35                  40                  45

Lys Asn Leu Ile Pro Phe Arg Pro Ser Ile Gln Phe Gln Gly Leu His
     50                  55                  60

Gly Leu Val Lys Ile Pro Lys Asn Asp Pro Leu Asn Glu Val His Asn
 65                  70                  75                  80

Phe Asn Phe Tyr Leu Ser Asn Val Gly Lys Asp Asn Pro Gln Gly Ser
                 85                  90                  95

Phe Asp Cys Ile Gln Gln Thr Phe Ser Ser Ser Gly Ala Ser Gln Leu
            100                 105                 110

Asn Cys Leu Gly Phe Ile Gln Asp Lys Ile Thr Val Cys Ala Thr Asn
        115                 120                 125

Asp Ser Tyr Gln Met Thr Arg Glu Arg Met Thr Gln Ala Glu Glu Glu
    130                 135                 140

Ser Arg Asn Arg Ser Thr Lys Val Ile Lys Pro Gly Gly Pro Tyr Val
145                 150                 155                 160

Gly Lys Arg Val Gln Ile Arg Lys Ala Pro Gln Ala Val Ser Asp Thr
                165                 170                 175

Val Pro Glu Arg Lys Arg Ser Thr Pro Met Asn Pro Ala Asn Thr Ile
            180                 185                 190

Arg Lys Thr His Ser Ser Ser Thr Ile Ser Gln Arg Pro Tyr Arg Asp
        195                 200                 205

Arg Val Ile His Leu Leu Ala Leu Lys Ala Tyr Lys Lys Pro Glu Leu
    210                 215                 220

Leu Ala Arg Leu Gln Lys Asp Gly Val Asn Gln Lys Asp Lys Asn Ser
225                 230                 235                 240

Leu Gly Ala Ile Leu Gln Gln Val Ala Asn Leu Asn Ser Lys Asp Leu
                245                 250                 255

Ser Tyr Thr Leu Lys Asp Tyr Val Phe Lys Glu Leu Gln Arg Asp Trp
            260                 265                 270

Pro Gly Tyr Ser Glu Ile Asp Arg Arg Ser Leu Glu Ser Val Leu Ser
        275                 280                 285

Arg Lys Leu Asn Pro Ser Gln Asn Ala Thr Gly Thr Ser Arg Ser Glu
    290                 295                 300

Ser Pro Val Cys Ser Ser Arg Asp Ala Val Ser Ser Pro Gln Lys Arg
305                 310                 315                 320

Leu Leu Asp Ser Glu Phe Ile Asp Pro Leu Met Asn Lys Lys Ala Arg
                325                 330                 335

Ile Ser His Leu Thr Asn Arg Val Pro Pro Thr Leu Asn Gly His Leu
            340                 345                 350

Asn Pro Thr Ser Glu Lys Ser Ala Ala Gly Leu Pro Leu Pro Pro Ala
        355                 360                 365

Ala Ala Ala Ile Pro Thr Pro Pro Pro Leu Pro Ser Thr Tyr Leu Pro
    370                 375                 380

Ile Ser His Pro Pro Gln Ile Val Asn Ser Asn Ser Asn Ser Pro Ser
385                 390                 395                 400

Thr Pro Glu Gly Arg Gly Thr Gln Asp Leu Pro Val Asp Ser Phe Ser
                405                 410                 415
```

-continued

```
Gln Asn Asp Ser Ile Tyr Glu Asp Gln Gln Asp Lys Tyr Thr Ser Arg
            420                 425                 430

Thr Ser Leu Glu Thr Leu Pro Pro Gly Ser Val Leu Leu Lys Cys Pro
        435                 440                 445

Lys Pro Met Glu Glu Asn His Ser Met Ser His Lys Lys Ser Lys Lys
    450                 455                 460

Lys Ser Lys Lys His Lys Glu Lys Asp Gln Ile Lys Lys His Asp Ile
465                 470                 475                 480

Glu Thr Ile Glu Glu Lys Glu Glu Asp Leu Lys Arg Glu Glu Glu Ile
                485                 490                 495

Ala Lys Leu Asn Asn Ser Ser Pro Asn Ser Ser Gly Gly Val Lys Glu
            500                 505                 510

Asp Cys Thr Ala Ser Met Glu Pro Ser Ala Ile Glu Leu Pro Asp Tyr
        515                 520                 525

Leu Ile Lys Tyr Ile Ala Ile Val Ser Tyr Glu Gln Arg Gln Asn Tyr
    530                 535                 540

Lys Asp Asp Phe Asn Ala Glu Tyr Asp Glu Tyr Arg Ala Leu His Ala
545                 550                 555                 560

Arg Met Glu Thr Val Ala Arg Arg Phe Ile Lys Leu Asp Ala Gln Arg
                565                 570                 575

Lys Arg Leu Ser Pro Gly Ser Lys Glu Tyr Gln Asn Val His Glu Glu
            580                 585                 590

Val Leu Gln Glu Tyr Gln Lys Ile Lys Gln Ser Ser Pro Asn Tyr His
        595                 600                 605

Glu Glu Lys Tyr Arg Cys Glu Tyr Leu His Asn Lys Leu Ala His Ile
    610                 615                 620

Lys Arg Leu Ile Gly Glu Phe Asp Gln Gln Gln Ala Glu Ser Trp Ser
625                 630                 635                 640
```

(2) INFORMATION FOR SEQ ID NO:3:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

CAATTAACCC TCATAAAGGG AAC 23

(2) INFORMATION FOR SEQ ID NO:4:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

CAAAGTTTCA CCTTTTAGAA TCTAGAGCAA CTC 33

(2) INFORMATION FOR SEQ ID NO:5:

(i) SEQUENCE CHARACTERISTICS:
(A) LENGTH: 42 base pairs
(B) TYPE: nucleic acid

-continued (C) STRANDEDNESS: single
(D) TOPOLOGY: linear (ii) MOLECULE TYPE: cDNA (xi) SEQUENCE DESCRIPTION: SEQ ID NO:5:

GAGGTGTCGA CGAGGAGCAG CGCTATGGGC TGTCGTGCGG AC 42

(2) INFORMATION FOR SEQ ID NO:6:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:6:

GTGTGGATCC TCATCACTAG GACCATGACT CTGCTTGCTG TTG 43

(2) INFORMATION FOR SEQ ID NO:7:

(i) SEQUENCE CHARACTERISTICS:
(A) LENGTH: 621 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:7:

```
Met Ala Ala Leu Lys Glu Asp Arg Ser Tyr Gly Leu Ser Gly Gly Arg
1               5                   10                  15

Val Ser Asp Gly Ser Lys Val Ser Val Phe His Val Lys Leu Thr Asp
            20                  25                  30

Ser Ala Ile Arg Ala Phe Glu Ser Tyr Arg Ala Arg Gln Asp Ser Val
        35                  40                  45

Ser Leu Arg Pro Ser Ile Arg Phe Gln Gly Ser Gln Gly His Ile Ser
    50                  55                  60

Ile Pro Gln Pro Asp Cys Pro Ala Glu Ala Arg Thr Phe Ser Phe Tyr
65                  70                  75                  80

Leu Ser Asn Ile Gly Arg Asp Asn Pro Gln Gly Ser Phe Asp Cys Ile
                85                  90                  95

Gln Gln Tyr Val Ser Ser His Gly Glu Val His Leu Asp Cys Leu Gly
            100                 105                 110

Ser Ile Gln Asp Lys Ile Thr Val Cys Ala Thr Asp Asp Ser Tyr Gln
        115                 120                 125

Lys Ala Arg Gln Ser Met Ala Gln Ala Glu Glu Glu Ile Arg Ser Arg
    130                 135                 140

Ser Ala Ile Val Ile Lys Ala Gly Gly Arg Tyr Leu Gly Lys Lys Val
145                 150                 155                 160

Gln Phe Arg Lys Pro Ala Pro Gly Ala Thr Asp Ala Val Pro Ser Arg
                165                 170                 175

Lys Arg Ala Thr Pro Ile Asn Leu Ala Ser Ala Ile Arg Lys Ser Gly
            180                 185                 190

Ala Ser Ala Val Ser Gly Gly Ser Gly Val Ser Gln Arg Pro Tyr Arg
        195                 200                 205

Asp Arg Val Ile His Leu Leu Ala Leu Arg Pro Tyr Arg Lys Ala Glu
    210                 215                 220
```

-continued

```
Leu Leu Leu Arg Leu Gln Lys Asp Gly Leu Thr Gln Ala Asp Lys Asp
225                 230                 235                 240

Ala Leu Asp Gly Ile Leu Gln Gln Val Ala Asn Met Ser Ala Lys Asp
                245                 250                 255

Gly Thr Cys Thr Leu Gln Asp Cys Met Tyr Lys Asp Val Gln Lys Asp
            260                 265                 270

Trp Pro Gly Tyr Ser Glu Gly Asp Gln Gln Leu Leu Lys Arg Val Leu
        275                 280                 285

Val Arg Lys Leu Cys Gln Pro Gln Ser Thr Gly Ser Leu Leu Gly Asp
    290                 295                 300

Pro Ala Ala Ser Ser Pro Pro Gly Glu Arg Gly Arg Ser Ala Ser Pro
305                 310                 315                 320

Pro Gln Lys Arg Leu Gln Pro Pro Leu Phe Ile Asp Pro Leu Ala Asn
                325                 330                 335

Lys Lys Pro Arg Ile Ser His Phe Thr Gln Arg Ala Gln Pro Ala Val
            340                 345                 350

Asn Gly Lys Leu Gly Val Pro Asn Gly Arg Glu Ala Leu Leu Pro Thr
        355                 360                 365

Pro Gly Pro Pro Ala Ser Thr Asp Thr Leu Ser Ser Ser Thr His Leu
    370                 375                 380

Pro Pro Arg Leu Glu Pro Pro Arg Ala His Asp Pro Leu Ala Asp Val
385                 390                 395                 400

Ser Asn Asp Leu Gly His Ser Gly Arg Asp Cys Glu His Gly Glu Ala
                405                 410                 415

Ala Ala Pro Ala Pro Thr Val Arg Leu Gly Leu Pro Leu Leu Thr Asp
            420                 425                 430

Cys Ala Gln Pro Ser Arg Pro His Gly Ser Pro Ser Arg Ser Lys Pro
        435                 440                 445

Lys Lys Lys Ser Lys Lys His Lys Asp Lys Glu Arg Ala Ala Glu Asp
    450                 455                 460

Lys Pro Arg Ala Gln Leu Pro Asp Cys Ala Pro Ala Thr His Ala Thr
465                 470                 475                 480

Pro Gly Ala Pro Ala Asp Thr Pro Gly Leu Asn Gly Thr Cys Ser Val
                485                 490                 495

Ser Ser Val Pro Thr Ser Thr Ser Glu Thr Pro Asp Tyr Leu Leu Lys
            500                 505                 510

Tyr Ala Ala Ile Ser Ser Ser Glu Gln Arg Gln Ser Tyr Lys Asn Asp
        515                 520                 525

Phe Asn Ala Glu Tyr Ser Glu Tyr Arg Asp Leu His Ala Arg Ile Glu
    530                 535                 540

Arg Ile Thr Arg Arg Phe Thr Gln Leu Asp Ala Gln Leu Arg Gln Leu
545                 550                 555                 560

Ser Gln Gly Ser Glu Glu Tyr Glu Thr Thr Arg Gly Gln Ile Leu Gln
                565                 570                 575

Glu Tyr Arg Lys Ile Lys Lys Thr Asn Thr Asn Tyr Ser Gln Glu Lys
            580                 585                 590

His Arg Cys Glu Tyr Leu His Ser Lys Leu Ala His Ile Lys Arg Leu
        595                 600                 605

Ile Ala Glu Tyr Asp Gln Arg Gln Leu Gln Ala Trp Pro
    610                 615                 620
```

-continued (2) INFORMATION FOR SEQ ID NO:8:

(i) SEQUENCE CHARACTERISTICS:
(A) LENGTH: 108 amino acids
(B) TYPE: amino acid
(C) STRANDEDNESS: Not Relevant
(D) TOPOLOGY: Not Relevant (ii) MOLECULE TYPE: protein (xi) SEQUENCE DESCRIPTION: SEQ ID NO:8:

```
Asp Trp Ile Arg Glu Tyr Pro Pro Ile Thr Ser Asp Gln Gln Arg Gln
1               5                   10                  15

Leu Tyr Lys Arg Asn Phe Asp Thr Gly Leu Gln Glu Tyr Lys Ser Leu
            20                  25                  30

Gln Ser Glu Leu Asp Glu Ile Asn Lys Glu Leu Ser Arg Leu Asp Lys
        35                  40                  45

Glu Leu Asp Asp Tyr Arg Glu Glu Ser Glu Glu Tyr Met Ala Ala Ala
    50                  55                  60

Asp Glu Tyr Asn Arg Leu Lys Gln Val Lys Gly Ser Ala Asp Tyr Lys
65                  70                  75                  80

Ser Lys Lys Asn His Cys Lys Gln Leu Lys Ser Lys Leu Ser His Ile
                85                  90                  95

Lys Lys Met Val Gly Asp Tyr Asp Arg Gln Lys Thr
            100                 105
```

(2) INFORMATION FOR SEQ ID NO:9:

(i) SEQUENCE CHARACTERISTICS:
(A) LENGTH: 297 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:9:

```
CTCCACCGCT GCCTTCAACC TATCTGCCCA TCTCACATCC TCCTCAGATT GTAAATTCTA     60

ACTCCAACTC CCCTAGCACT CCAGAAGGCC GGGGGACTCA AGACCTACCT GTTGACAGTT    120

TTAGTCAAAA CGATAGTATC TATGAGGACC AGCAAGACAA ATATACCTCT AGGACTTCTC    180

TGGAAACCTT ACCCCCTGGT TCCGTTCTAC TAAAGTGTCC AAAGCCTATG GAAGAAAACC    240

ATTCAATGTC TCACAAAAAG TCCAAAAAGA AGTCTAAAAA ACATAAGGAA AAGGACC       297
```

(2) INFORMATION FOR SEQ ID NO:10:

(i) SEQUENCE CHARACTERISTICS:
(A) LENGTH: 358 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:10:

```
CGCAACCGAA GCACAAAAGT TATCAAACCC GGTGGACCAT ATGTAGGGAA AAGAGTGCAA     60

ATTCGGAAAG CACCTCAAGC TGTTTCAGAT ACAGTTCCTG AGAGGAAAAG GTCAACCCCC    120

ATGAACCCTG CAAATACAAT TCGAAAGACA CATAGCAGCA GCACCATCTC TCAGAGGCCA    180

TACAGGGACA GGGTGATTCA NTTACTGGCC CTGAAGGCCT ACAAGAAACC GGAGCTACTT    240
```

-continued

```
GCTAGACTCC AGAAAGATGG TGTCAATCAA AAAGACAAGA ACTCCCTGGG GAGGCAATTN    300

TTGCAACAGG TAGNCCAATC TGGATTTCTA AGGGACCTCT TCATATTACC TTTAAAGG      358
```

(2) INFORMATION FOR SEQ ID NO:11:

(i) SEQUENCE CHARACTERISTICS:
(A) LENGTH: 362 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:11:

```
AGCGNCGTNN TCGNCGGGCA CCCCGGGGAG TTTGAAGATG GCGGCGGGGG GGACAGGGGG     60

CCTNCGGGAG GAGCAGCGCT ATGGGCTGTC GTGCCGGACG GCTGGGGCAG GACAACATCA    120

CCGTACTGCA TGTNAAAGCT TCACCGAGAC GGNCGATTCC GGGGCGGTTC GAGAACTTAC    180

CAGAGCCACA AGNNTTTNAA TTCCCTTTTC GGACCTTCAA TCCAGTTTCC AAGGACTCCA    240

CGGGCTTTGT NCAAAAATTT CCCAAAAATG ATTCCCCTTC AATGGANAGT TCATAAATTT    300

TAAATTTTTA ATTTGTTCAA ATNTTGGGGN AAAGNCAAAC CTTCAAGGGC NAGTTTTGGA    360

CT                                                                   362
```

(2) INFORMATION FOR SEQ ID NO:12:

(i) SEQUENCE CHARACTERISTICS:
(A) LENGTH: 477 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:12:

```
AATTCGGCAC GAGCATGGTC CTAGAACTCT GCTTNGACCA GAAGATGTGA ATAAACTTAA     60

GCTTATTTAT TTAAAATTCC AAATGAGTTN NTCTAGNTTC TAAAAAGGTG AAACTTTGGC    120

TGTTGAAAGT TTCAGTATTA GTAAACTTGA GTTACTTTNN CTTTTCCATT TNACTTTGCT    180

TCCCTGCATT TCGAAGCTGC TCTTTCTGGT CCTCCCCACC ACCCCACCCC CAAGACTTGT    240

GTTTGTTAAT AGAAATAATT TTTTTAGGTA TTGGGGATCC ATTGTCTATT ATTTCAAATC    300

AAGNTTTTTN TTTNTCCTCA AAAANCTTGT GGTTTTGTGA TTAGGAAATG GNTTTTTTAG    360

ATATTGGGGN TCCAGTGTCC NCACTTGAAA AGGTGGGNAG GGGTTTAAAA AANAGCANCA    420

GTAATNTGCA AGGTGNAATG NTTTTGGTNA ACGGANGCCA TTTTCCGACG TNCTTAA       477
```

(2) INFORMATION FOR SEQ ID NO:13:

(i) SEQUENCE CHARACTERISTICS:
(A) LENGTH: 178 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:13:

```
AAACATTCTC CAGCTCTGGG ACCTCCCANC TCAATTCCCT GGGAATTNAT ACAAGATAAA     60

ATTACAGTGT GTGCACAAAC GACTCGTATC AAATGACACG AGAAANANTG ACCCAGGCAG    120

NGGAGGGAAT CCCGCAACCA ANGCACAAAA GTTATTCAAA CCCGGTGGGA CCATATNT      178
```

-continued (2) INFORMATION FOR SEQ ID NO:14:

(i) SEQUENCE CHARACTERISTICS:
(A) LENGTH: 158 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:14:

GNCCTTTCTC CANTCTCAAA AGNGNTATCA CAATGTTCAT GNAAGAAGTC TTACAAGAAT 60

ATCAGAAGAT AAAGCCAGTC TAGTCCCAAT TACCATGAAG NAAAAATACA GATGTGNAAT 120

ATCTTCATAA CAAGCTGGCT CACATCAAAA GGCTAATN 158

(2) INFORMATION FOR SEQ ID NO:15:

(i) SEQUENCE CHARACTERISTICS:
(A) LENGTH: 438 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:15:

ATAAATAAGC TTAAGTTTAT TCACATCTTC TGGTCCAAGC AGAGTTCTAG GACCATGACT 60

CTGCTTGCTG TTGGTCAAAT TCACCTATTA GCCTTTTGAT GTGAGCCAGC TTGTTATGAA 120

GATATTCACA TCTGTATTTT TCTTCATGGT AATTGGGACT AGACTGCTTT ATCTTCTGAT 180

ATTCTTGTAA GACTTCTTCA TGAACATTCT GATACTCTTT TGAGCCTGGA GAAAGGCGCT 240

TTCTTTGTGC ATCTAGTTTG ATAAATCTTC TAGCTACAGT CTCCATCCTG GCATGCAAAG 300

CTCTGTACTC ATCATACTCT GCATTGAAGT CATCCTTATA ATTCTGGCGT TGCTCATAGG 360

AGACGATAGC GATATATTTT ATCAAATAAT CTGGGAGTTC AATTGCTGAA GGGTCCATGG 420

AGGCAGTGCA ATCCTCTT 438

(2) INFORMATION FOR SEQ ID NO:16:

(i) SEQUENCE CHARACTERISTICS:
(A) LENGTH: 459 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:16:

GCGNCCGCAG TGGANGGCTA GAGCGNAGCG CGCGGCGGCG GNCACCCCGG GGAGTTTAAG 60

ATGGCGGCNG GGGGGACAGG GGGCCTGCGG GAGGAGCAGC GCTATGGGCT GTCGTGCGGA 120

CGGCTGGGGC AGGACAACAT CACCGTACTG CATGTGAAGC TCACCGAGAC GGCGATCCGG 180

GCGCTCGAGA CTTACCAGAG CCACAAGAAT TTAATTCCTT TTCGACCTTC AATCCAGTTC 240

CAAGGACTCC ACGGGCTTGT CAAAATTCCC AAAAATGATC CCCTCAATGA AGTTCATAAC 300

TTTAACTTTT ATTTGTCAAA TGTGGGCAAA GACAACCCTC AGGGCAAGCT TTGACTGCAT 360

CCAGCAAACA TTCTCCAGCT CTGGAGCCTC CCAGCTCAAT TGCCTNGGGA TTTATACAAG 420

ATAAAATTAC AGTGTGTGCA ACAAACGACT CGTATCAGA 459

-continued (2) INFORMATION FOR SEQ ID NO:17:

(i) SEQUENCE CHARACTERISTICS:
(A) LENGTH: 412 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:17:

TGGGATTCAA ATGACCATTT AGTGTTGGTG GTACTCTGTT CGTCAGGTGA GATATTCGGG 60

CTTTTTTATT CATTAAAGGA TCAATAAACT CTGAATCCAA AAGCCGTTTC TGAGGAGAAG 120

ATACAGCATC TCTACTAGAA CATACAGGAG ATTCTGAACG GCTGGTGCCT GTAGCATTCT 180

GAGACGGATT TAGTTTTCTA GAGAGCACTG ACTCCAATGA CCGTCTGTCT ATTTCACTGT 240

ATCCAGGCCA GTCTCTTTGA AGCTCTTTAA AAACATAATC CTTTAAGGGA TATGAGAGGT 300

CCTTAGAATT CAGATTGGCT AGCTGTTGCA GAATTGCTCC CAGGGAGTTC TTGTCTTTTT 360

GATTGACACC ATCTTTCTGG AGTCCTACAA GTAGCTCCGG GTTTCTTGTA GG 412

(2) INFORMATION FOR SEQ ID NO:18:

(i) SEQUENCE CHARACTERISTICS:
(A) LENGTH: 487 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:18:

CCAAATAAAG AAACTTGACA TTGAGACCAT GGAGGAGAAG GAGGAAGACC TTCAGAGAGA 60

AGAAACTGCC AAGCTGAGTA ATGCCAGTCC AAATCCCAAT GAAGGAGTTA AAGAAGGGTG 120

CACAGCCTCC ATGGAGCCTT CTTCAGCACT TGAACTCCCA GATTATTTGA TAAAATATAT 180

TGCTATTGTC TCTTATGAGC AACGCCAGAA TTACAAGGAT GACTTCAATG CTGAGTATGA 240

TGAATACAGA GCTTTGCATG CAAGGATGGA GACTGTAGCC AGGAGATTTA TTAAACTGGA 300

TGCACAACGA AAACGCCTTT CTCCAGGTTC AAAAGAGTAC CAGAATGTTC ATGAAGAAGT 360

CTTACAGGAA TATCAGAAGA TCAAGCAGTC CAGTCCCAAT TACCATGAAG AAAAATACAG 420

ATGTGAATAT CTTCATAACA AGCTGGCTCA CATCAAAGAC TAATAGGTCG AATTTGACCA 480

ACAGCAA 487

(2) INFORMATION FOR SEQ ID NO:19:

(i) SEQUENCE CHARACTERISTICS:
(A) LENGTH: 525 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:19:

GCTTTGCATG CCAGGATGGA GACTGTAGCT AGAAGATTTA TCAAACTAGA TGCACAAAGA 60

AAGCGCCTTT CTCCAGGCTC AAAAGAGTAT CAGAATGTTC ATGAAGAAGT CTTACAAGAA 120

TATCAGAAGA TAAAGCAGTC TAGTCCCAAT TACCATGAAG AAAAATACAG ATGTGAATAT 180

CTTCATAACA AGCTGGCTCA CATCAAAAGG CTAATAGGTG AATTTGACCA ACAGCAAGCA 240

GAGTCATGGT CCTAGAACTC TGCTTGGACC AGAAGATGTG AATAAACTTA AGCTTATTTA 300

-continued

```
TTTAAAATTC CAAATGAGTT GCTCTAGATT CTAAAAAGGT GAAACTTTGG CTGTTGAAAG    360

TTTCAGTATT AGTAAACTTN GAGTTACTTT TTCTTTTCCA TTTTACTTTG CTTCCCTGCA    420

TTTCGGAAGC TGCCTCTTTN CTGGGTCCTC NCCACTNGGG GCCAGCCCCC AAGNACTTGG    480

TGTTTTGGTT AATAGGNAAT AATTTTCTTT AAGGGAATTG GGGGA                    525
```

(2) INFORMATION FOR SEQ ID NO:20:

(i) SEQUENCE CHARACTERISTICS:
(A) LENGTH: 455 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:20:

```
TTAGTCAAAA TGGTAGCATC TTTGAGGACC AGCAAGAAAA ATATACCTCA AGGACTTGTC     60

TGGAAACATT ACCCCCCAGC TCAGCTCTGC TAAAGTGTCC AAAGCCCATG GAAGAAGAGC    120

ATCCAGTGTC TCACAAAAAG TCCAAAAAGA AGTCTAAAAA ACACAAGGAA AAGGACCAAA    180

TAAAGAAACT TGACATTGAG ACCATGGAGG AGAAGGAGGA AGACCTTCAG AGAGAAGAAA    240

CTGCCAAGCT GAGTAATGCC AGTCCAAATC CCAATGAAGG AGTTAAAGAA GGGTGCACAG    300

CCTCCATGGA GCCTTCTTCA GCACTTGAAC TCCCAGATTA TTTGATAAAA TATATTGCTA    360

TTGTCTCTTA TGAGCAACGC CAGAATTACA AGGATGACTT CAATGCTGAG TATGATGAAT    420

ACAGAGCTTT GCATGCAAGG ATGGAGACTG TAGCG                               455
```

(2) INFORMATION FOR SEQ ID NO:21:

(i) SEQUENCE CHARACTERISTICS:
(A) LENGTH: 379 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:21:

```
TCACTTACTG GCCCTGAAGG CTACAAGAAA CCGGAGCTAC TTGCTAGACT CCAGAAAGAT     60

GGTGTCAATC AAAAAGACAA GAACTCCCTG GGAGCAATTC TGCAACAGGT AGCCAATCTG    120

AATTCTAAGG ACCTCTCATA TACCTTAAAG GATTATGTTT TTAAAGAGCT TCAAAGAGAC    180

TGGCCTGGNT ACAGTGAAAT AGACAGACGG TCATTGGAGT CAGTGCTCTC TAGAAAACTA    240

AATCCGTCTC AGAATGCTAC AGGCACCAGC CTNTCAGAAT CTCCTGTATG TTCTAGTAGA    300

GATGCTGTAT CTTCTCCTCA GGAAACGGCT TTTGGGTTTC AGAGTTTATT TGATCCCTTT    360

AATGGANTTA AAAAAGGCT                                                 379
```

(2) INFORMATION FOR SEQ ID NO:22:

(i) SEQUENCE CHARACTERISTICS:
(A) LENGTH: 519 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:22:

```
NTCACTTACT GGCCCTGAAG CTANCAAGAA ACCGGAGCTA CTTGCTAGAC TCCAGAAAGA     60
```

-continued

TGGTGTCAAT CAAAAAGACA AGAACTCCCT GGGAGCAATT CTGCAACAGG TAGCCAATCT 120

GAATTCTAAG GACCTCTCAT ATACCTTAAA GGATTATGTT TTTAAAGAGC TTCAAAGAGA 180

CTGGCCTGGG ATACAGTGAA ATAGACAGAC GGTCATTGGA GTCAGTGCTC TCTAGAAAAC 240

TAAATCCGTC TCAGAATGCT ACAGGCACCA GCGTTTCAGA ATCTCCTGTA TGTTCTAGTA 300

GGAGATGCTG TATCTTCTCC TCAGGAAACG GCTTTTGGGT TCAGGAGTTT ATTTGATCCN 360

TTTAATGGAT TAAAAAAGGC CCCGATTATT CTTCACCTGG ACGGAACAGA GTTACCNCCC 420

AACATTAATG GGTCCNTTTG GATTCCCACC AGTGGAAAAT TGGGTGGCGG GCTTNCCCAT 480

TGCCCCTGNG GGTGGTGGCN TTCCCCACCC TTNCACCGG 519

(2) INFORMATION FOR SEQ ID NO:23:

(i) SEQUENCE CHARACTERISTICS:
(A) LENGTH: 297 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:23:

CTCCACCGCT GCCTTCAACC TATCTGCCCA TCTCACATCC TCCTCAGATT GTAAATTCTA 60

ACTCCAACTC CCCTAGCACT CCAGAAGGCC GGGGGACTCA AGACCTACCT GTTGACAGTT 120

TTAGTCAAAA CGATAGTATC TATGAGGACC AGCAAGACAA ATATACCTCT AGGACTTCTC 180

TGGAAACCTT ACCCCCTGGT TCCGTTCTAC TAAAGTGTCC AAAGCCTATG GAAGAAAACC 240

ATTCAATGTC TCACAAAAAG TCCAAAAAGA AGTCTAAAAA ACATAAGGAA AAGGACC 297

(2) INFORMATION FOR SEQ ID NO:24:

(i) SEQUENCE CHARACTERISTICS:
(A) LENGTH: 358 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:24:

CGCAACCGAA GCACAAAAGT TATCAAACCC GGTGGACCAT ATGTAGGGAA AAGAGTGCAA 60

ATTCGGAAAG CACCTCAAGC TGTTTCAGAT ACAGTTCCTG AGAGGAAAAG GTCAACCCCC 120

ATGAACCCTG CAAATACAAT TCGAAAGACA CATAGCAGCA GCACCATCTC TCAGAGGCCA 180

TACAGGGACA GGGTGATTCA NTTACTGGCC CTGAAGGCCT ACAAGAAACC GGAGCTACTT 240

GCTAGACTCC AGAAAGATGG TGTCAATCAA AAAGACAAGA ACTCCCTGGG GAGGCAATTN 300

TTGCAACAGG TAGNCCAATC TGGATTTCTA AGGGACCTCT TCATATTACC TTTAAAGG 358

(2) INFORMATION FOR SEQ ID NO:25:

(i) SEQUENCE CHARACTERISTICS:
(A) LENGTH: 285 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:25:

TTTTGTGAGA CATTGAATGG TTTTCTTCCA TAGGCTTTGG ACACTTTAGT AGAACGGAAC 60

-continued

CAGGGGGTAA GGTTTCCAGA GAAGTCCTAG AGGTATATTT GTCTTGCTGG TCCTCATAGA 120

TACTATCGTT TTGACTAAAA CTNTCAACAG GTAGGTCTTG AGTCCCCCGG CCTTCTGGAG 180

TGCTAGGGGA GTTGGAGTTA GAATTTACAA TCTGAGGAGG ATGTGAGATG GGCAGATAGG 240

TTGAAGGCAG CGGTGGAGGG GTGGGGATGG CAGCAGCCCA GGGGG 285

(2) INFORMATION FOR SEQ ID NO:26:

(i) SEQUENCE CHARACTERISTICS:
(A) LENGTH: 431 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:26:

TTTATTCCAA ACAGCATCAT CTACAACTCA TAATCGCAGG CTCCTCCAGT TCATTTAACA 60

CAGAAAGCAG GCTTTTTTCT CTTTTCCCAT TTAAACAAAT GTAAAATACC TTCATTGGGA 120

TTTGGACTGG CATTACTCAG CTTGGCAGTT TCTTCTCTCT GAAGGTCTTC CTCCTTCTCC 180

TCCATGGTCT CAATGTCAAG TTTCTTTATT TGGTCCTTTT CCTTGTGTTT TTTAGACTTC 240

TTTTTGGACT TTTTGTGAGA CACTGGATGC TCTTCTTCCA TGGGCTTTGG ACACTTTAGC 300

AGAGTGAGCT GGGGGGTAAT GTTTCCAGAC AAGTCCTTGA GGTATATTTT TCTTGCTGGT 360

CCTCAAAGAT GCTACCATTT TGACTAAAAC TGTCAACAGG CAGGTCTTGA GTCCCAGGCC 420

TTCTGGAGTG C 431

(2) INFORMATION FOR SEQ ID NO:27:

(i) SEQUENCE CHARACTERISTICS:
(A) LENGTH: 196 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:27:

CACCGAGACG GCGATCCGGG CGCTCGAGAC TTACCAGAGC CACAAGAATT TAATTCCTTT 60

TCGACCTTCA ATCCAGTTCC AAGGACTCCA CGGGCTTGTC AAAATTCCCA AAAATGATCC 120

CCTCAATGAA GTTCATAACT TTAACTTTTA TTTGTCAAAT GTGGGCAAAG ACAACCCTCA 180

GGGGAGCTTG GGCTGC 196

(2) INFORMATION FOR SEQ ID NO:28:

(i) SEQUENCE CHARACTERISTICS:
(A) LENGTH: 197 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:28:

ACCATCTCTC AGAGGCCATA CAGGGACAGG GTGATTCACT TACTGGCCCT GAAGGCNTAC 60

AAGAAACCGG AGCTACTTGC TAGACTCCAG AAAGATGGTG TCAATCAAAA AGACAAGAAC 120

TCCCTGGGAG CAATTCTGCA ACAGGTAGCC AATCTGAATN CTAAGGACCT CNTCATATAC 180

CTTAAAGGAT TATGTTT 197

-continued (2) INFORMATION FOR SEQ ID NO:29:

(i) SEQUENCE CHARACTERISTICS:
(A) LENGTH: 348 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:29:

GCGCCCGGCA GTGGAGGCTA GAGCCGCAGC GCGCGGCGGG CGGACACCGC CGGGGAGGTT 60

TAAGAGTGGC GGCTGGGGGG GACAGGGGGG CCTGCAGGGA GGAGCAGCGC TATGGGCTGT 120

CGTGCGGACG GCGTGGGGCA GGACAACATC ACCGTACTGC ATGTGAAGCT CACCGAGACG 180

GCGATCCGGG CGCTCGAGAC TTACCAGAGC CACAAGAATT TAATTCCTTT TCGACCTTCA 240

ATCCAGTTCC AAGGACTCCA CGGGGTGAGT ACTCTTATTG ATTTAACAAA CAAATCTAAT 300

GTTCTTGCAC GCTATTCAAC TTTTAAAATC CGTTTTCAGT TGACCCTT 348

(2) INFORMATION FOR SEQ ID NO:30:

(i) SEQUENCE CHARACTERISTICS:
(A) LENGTH: 184 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:30:

GGAATTTTAA ATAAATAAGC TTAAGTTTAT TCACATCTNC TGGTCCAAGC AGAGTTCTAG 60

GACCATGACT CTGCTTGCTG TTGGTCAAAT TCACCTATTA GCCTTTNGAT GTGAGCCAGC 120

TTGTTATGAA GATATTCACA TCTGTATTTT NCTTCATGGT AATTGGGACT AGACTGCTTT 180

ATCT 184

(2) INFORMATION FOR SEQ ID NO:31:

(i) SEQUENCE CHARACTERISTICS:
(A) LENGTH: 280 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:31:

TCCTAGAACT CTGCTTGGAC CAGAAGATGT GAATAAACTT AAGCTTATTT ATTTAAAATC 60

ACAAATGAGT TGCTCTAGAT TCTAAAAGGG TGAAACTTTG ACTGTTGAAA GTTTAAGTAT 120

TAGTAAACTT GAGTTACTTT TTCTTTCAAA TTTCACTCCG CTTCCCTGCA TTTCGAAGCT 180

GCTCTTTCTG GTCCTACCCA CCACCCCACC AACAAGACTT GTGTTTGTTA ATAGAAATAA 240

TTTATCAAGG TATTGGGGAT CCATTGTCTA TATTTAAAAC 280

(2) INFORMATION FOR SEQ ID NO:32:

(i) SEQUENCE CHARACTERISTICS:
(A) LENGTH: 255 base pairs
(B) TYPE: nucleic acid
(C) STRANDEDNESS: both
(D) TOPOLOGY: both (ii) MOLECULE TYPE: cDNA -continued (xi) SEQUENCE DESCRIPTION: SEQ ID NO:32:

AACTAGCAGT CCCTTTGGGC CAATTGATGT AATTATTTTC AGTGTAAATC CNAAAGGTTG 60

CCTGTTTTAN GNTAGGAGAT GATAGTAAAA ATACCTAATG CTCTGTTTTT ATACCTCATA 120

CTAGGTAGCC AATCTGAATT CTAAGGACCT CTCATATACC TTAAAGGATT ATGTTTNTAA 180

AGAGCTTCAA AGAGACTGGC CTGGATACAG TGAAATAGAC AGACGGTCAT TGGAGTCATG 240

TGCTCTCTAG GTGAA 255

(2) INFORMATION FOR SEQ ID NO:33:

(i) SEQUENCE CHARACTERISTICS:
(A) LENGTH: 3974 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:33:

GGTACCTAAG TGAGTAGGGC GTCCGATCGA CGGACGCCTT TTTTTTGAAT TCGTAATCAT 60

GGTCATAGCT GTTTCCTGTG TGAAATTGTT ATCCGCTCAC AATTCCACAC AACATACGAG 120

CCGGAAGCAT AAAGTGTAAA GCCTGGGGTG CCTAATGAGT GAGCTAACTC ACATTAATTG 180

CGTTGCGCTC ACTGCCCGCT TTCCAGTCGG GAAACCTGTC GTGCCAGCTG CATTAATGAA 240

TCGGCCAACG CGCGGGGAGA GGCGGTTTGC GTATTGGGCG CTCTTCCGCT TCCTCGCTCA 300

CTGACTCGCT GCGCTCGGTC GTTCGGCTGC GGCGAGCGGT ATCAGCTCAC TCAAAGGCGG 360

TAATACGGTT ATCCACAGAA TCAGGGGATA ACGCAGGAAA GAACATGTGA GCAAAAGGCC 420

AGCAAAAGGC CAGGAACCGT AAAAAGGCCG CGTTGCTGGC GTTTTTCCAT AGGCTCCGCC 480

CCCCTGACGA GCATCACAAA AATCGACGCT CAAGTCAGAG GTGGCGAAAC CCGACAGGAC 540

TATAAAGATA CCAGGCGTTT CCCCCTGGAA GCTCCCTCGT GCGCTCTCCT GTTCCGACCC 600

TGCCGCTTAC CGGATACCTG TCCGCCTTTC TCCCTTCGGG AAGCGTGGCG CTTTCTCATA 660

GCTCACGCTG TAGGTATCTC AGTTCGGTGT AGGTCGTTCG CTCCAAGCTG GGCTGTGTGC 720

ACGAACCCCC CGTTCAGCCC GACCGCTGCG CCTTATCCGG TAACTATCGT CTTGAGTCCA 780

ACCCGGTAAG ACACGACTTA TCGCCACTGG CAGCAGCCAC TGGTAACAGG ATTAGCAGAG 840

CGAGGTATGT AGGCGGTGCT ACAGAGTTCT TGAAGTGGTG GCCTAACTAC GGCTACACTA 900

GAAGAACAGT ATTTGGTATC TGCGCTCTGC TGAAGCCAGT TACCTTCGGA AAAAGAGTTG 960

GTAGCTCTTG ATCCGGCAAA CAAACCACCG CTGGTAGCGG TGGTTTTTTT GTTTGCAAGC 1020

AGCAGATTAC GCGCAGAAAA AAAGGATCTC AAGAAGATCC TTTGATCTTT TCTACGGGGT 1080

CTGACGCTCA GTGGAACGAA AACTCACGTT AAGGGATTTT GGTCATGAGA TTATCGTCGA 1140

CAATTCGCGC GCGAAGGCGA AGCGGCATGC ATTTACGTTG ACACCATCGA ATGGTGCAAA 1200

ACCTTTCGCG GTATGGCATG ATAGCGCCCG GAAGAGAGTC AATTCAGGGT GGTGAATGTG 1260

AAACCAGTAA CGTTATACGA TGTCGCAGAG TATGCCGGTG TCTCTTATCA GACCGTTTCC 1320

CGCGTGGTGA ACCAGGCCAG CCACGTTTCT GCGAAAACGC GGGAAAAAGT GGAAGCGGCG 1380

ATGGCGGAGC TGAATTACAT TCCCAACCGC GTGGCACAAC AACTGGCGGG CAAACAGTCG 1440

TTGCTGATTG GCGTTGCCAC CTCCAGTCTG GCCCTGCACG CGCCGTCGCA AATTGTCGCG 1500

GCGATTAAAT CTCGCGCCGA TCAACTGGGT GCCAGCGTGG TGGTGTCGAT GGTAGAACGA 1560

AGCGGCGTCG AAGCCTGTAA AGCGGCGGTG CACAATCTTC TCGCGCAACG CGTCAGTGGG 1620

-continued

```
CTGATCATTA ACTATCCGCT GGATGACCAG GATGCCATTG CTGTGGAAGC TGCCTGCACT   1680
AATGTTCCGG CGTTATTTCT TGATGTCTCT GACCAGACAC CCATCAACAG TATTATTTTC   1740
TCCCATGAAG ACGGTACGCG ACTGGGCGTG GAGCATCTGG TCGCATTGGG TCACCAGCAA   1800
ATCGCGCTGT TAGCGGGCCC ATTAAGTTCT GTCTCGGCGC GTCTGCGTCT GGCTGGCTGG   1860
CATAAATATC TCACTCGCAA TCAAATTCAG CCGATAGCGG AACGGGAAGG CGACTGGAGT   1920
GCCATGTCCG GTTTTCAACA AACCATGCAA ATGCTGAATG AGGGCATCGT TCCCACTGCG   1980
ATGCTGGTTG CCAACGATCA GATGGCGCTG GGCGCAATGC GCGCCATTAC CGAGTCCGGG   2040
CTGCGCGTTG GTGCGGATAT CTCGGTAGTG GGATACGACG ATACCGAAGA CAGCTCATGT   2100
TATATCCCGC CGTTAACCAC CATCAAACAG GATTTTCGCC TGCTGGGGCA AACCAGCGTG   2160
GACCGCTTGC TGCAACTCTC TCAGGGCCAG GCGGTGAAGG GCAATCAGCT GTTGCCCGTC   2220
TCACTGGTGA AAAGAAAAAC CACCCTGGCG CCCAATACGC AAACCGCCTC TCCCCGCGCG   2280
TTGGCCGATT CATTAATGCA GCTGGCACGA CAGGTTTCCC GACTGGAAAG CGGGCAGTGA   2340
GCGCAACGCA ATTAATGTAA GTTAGCGCGA ATTGTCGACC AAAGCGGCCA TCGTGCCTCC   2400
CCACTCCTGC AGTTCGGGGG CATGGATGCG CGGATAGCCG CTGCTGGTTT CCTGGATGCC   2460
GACGGATTTG CACTGCCGGT AGAACTCCGC GAGGTCGTCC AGCCTCAGGC AGCAGCTGAA   2520
CCAACTCGCG AGGGGATCGA GCCCGGGGTG GGCGAAGAAC TCCAGCATGA GATCCCCGCG   2580
CTGGAGGATC ATCCAGCCGG CGTCCCGGAA AACGATTCCG AAGCCCAACC TTTCATAGAA   2640
GGCGGCGGTG GAATCGAAAT CTCGTGATGG CAGGTTGGGC GTCGCTTGGT CGGTCATTTC   2700
GAACCCCAGA GTCCCGCTCA GAAGAACTCG TCAAGAAGGC GATAGAAGGC GATGCGCTGC   2760
GAATCGGGAG CGGCGATACC GTAAAGCACG AGGAAGCGGT CAGCCCATTC GCCGCCAAGC   2820
TCTTCAGCAA TATCACGGGT AGCCAACGCT ATGTCCTGAT AGCGGTCCGC CACACCCAGC   2880
CGGCCACAGT CGATGAATCC AGAAAAGCGG CCATTTTCCA CCATGATATT CGGCAAGCAG   2940
GCATCGCCAT GGGTCACGAC GAGATCCTCG CCGTCGGGCA TGCGCGCCTT GAGCCTGGCG   3000
AACAGTTCGG CTGGCGCGAG CCCCTGATGC TCTTCGTCCA GATCATCCTG ATCGACAAGA   3060
CCGGCTTCCA TCCGAGTACG TGCTCGCTCG ATGCGATGTT TCGCTTGGTG GTCGAATGGG   3120
CAGGTAGCCG GATCAAGCGT ATGCAGCCGC CGCATTGCAT CAGCCATGAT GGATACTTTC   3180
TCGGCAGGAG CAAGGTGAGA TGACAGGAGA TCCTGCCCCG GCACTTCGCC CAATAGCAGC   3240
CAGTCCCTTC CCGCTTCAGT GACAACGTCG AGCACAGCTG CGCAAGGAAC GCCCGTCGTG   3300
GCCAGCCACG ATAGCCGCGC TGCCTCGTCC TGCAGTTCAT TCAGGGCACC GGACAGGTCG   3360
GTCTTGACAA AAAGAACCGG GCGCCCCTGC GCTGACAGCC GGAACACGGC GGCATCAGAG   3420
CAGCCGATTG TCTGTTGTGC CCAGTCATAG CCGAATAGCC TCTCCACCCA AGCGGCCGGA   3480
GAACCTGCGT GCAATCCATC TTGTTCAATC ATGCGAAACG ATCCTCATCC TGTCTCTTGA   3540
TCAGATCTTG ATCCCCTGCG CCATCAGATC CTTGGCGGCA AGAAAGCCAT CCAGTTTACT   3600
TTGCAGGGCT TCCCAACCTT ACCAGAGGGC GCCCCAGCTG GCAATTCCGG TTCGCTTGCT   3660
GTCCATAAAA CCGCCCAGTC TAGCTATCGC CATGTAAGCC CACTGCAAGC TACCTGCTTT   3720
CTCTTTGCGC TTGCGTTTTC CCTTGTCCAG ATAGCCCAGT AGCTGACATT CATCCGGGGT   3780
CAGCACCGTT TCTGCGGACT GGCTTTCTAC GTGTTCCGCT TCCTTTAGCA GCCCTTGCGC   3840
CCTGAGTGCT TGCGGCAGCG TGAAGCTTAA AAAACTGCAA AAAATAGTTT GACTTGTGAG   3900
CGGATAACAA TTAAGATGTA CCCAATTGTG AGCGGATAAC AATTTCACAC ATTAAAGAGG   3960
AGAAATTACA TATG                                                     3974
```

-continued

```
(2) INFORMATION FOR SEQ ID NO:34:

     (i) SEQUENCE CHARACTERISTICS:
          (A) LENGTH: 112 base pairs
          (B) TYPE: nucleic acid
          (C) STRANDEDNESS: both
          (D) TOPOLOGY: both

    (ii) MOLECULE TYPE: cDNA

    (xi) SEQUENCE DESCRIPTION: SEQ ID NO:34:

AAGCTTAAAA AACTGCAAAA AATAGTTTGA CTTGTGAGCG GATAACAATT AAGATGTACC     60

CAATTGTGAG CGGATAACAA TTTCACACAT TAAAGAGGAG AAATTACATA TG            112
```

ELL2, A NEW MEMBER OF AN ELL FAMILY OF RNA POLYMERASE II ELONGATION FACTORS

The present application is a divisional of U.S. application Ser. No. 09/026,343, filed Feb. 19, 1998 (now U.S. Pat. No. 6,008,018), which is herein incorporated by reference; said 09/026,343 claims the benefit of U.S. Provisional Application No. 60/038,447, filed Feb. 19, 1997, which is herein incorporated by reference.

FIELD OF THE INVENTION

This invention relates to newly identified polynucleotides, polypeptides encoded by them and to the use of such polynucleotides and polypeptides, and to their production. More particularly, the polynucleotides and polypeptides of the present invention relate to a new member of an ELL family of RNA polymerase II elongation factors, hereinafter referred to as ELL2. The invention also relates to inhibiting or activating the action of such polynucleotides and polypeptides.

BACKGROUND OF THE INVENTION

The elongation stage of eukaryotic messenger RNA synthesis is a major site for the regulation of gene expression (Reines, D. et al., *Trends. Biochem. Sci.* 21:351–355 (1996), Bentley, D. L., *Curr. Opin. Genet. Dev.* 5:210–216 (1995)). Moreover, a growing body of evidence suggests that misregulation of elongation may be a key element in a variety of human diseases (Aso, T. et al., *J. Clin. Invest.* 97:1561–1569 (1996)).

To date, one virally encoded protein (Tat) and five cellular proteins (SII, P-TEFb, TFIIF, Elongin (SIII), and ELL) have been defined biochemically and shown to be capable of controlling the activity of the RNA polymerase II elongation complex. Among these elongation factors, three have been implicated in human disease. The HIV-1 encoded Tat protein is required for efficient transcription of HIV-1 genes and for productive infection by the virus (Jones, K. A. & Peterlin, B. M., *Annu. Rev. Biochem.* 63:717–743 (1994)). Elongin (SIII) is a potential target for regulation by the product of the von Hippel-Lindau (VHL) tumor suppressor gene, which is mutated in the majority of clear-cell renal carcinomas and in families with VHL disease, a rare genetic disorder that predisposes individuals to a variety of cancers (Duan, D. R. et al., *Science* 269:1402–1406 (1995), Kibel, A. et al., *Science* 269:1444–1446 (1995)). The ELL gene on chromosome 19pl3.1 was originally isolated as a gene that undergoes frequent translocations with the *Drosophila trithorax*-like MLL gene on chromosome 11q23 in acute myeloid leukemia (Thirman, M. J. et al., *Proc. Natl. Acad. Sci. U.S.A.* 91:12110–12114 (1994), Mitani, K. et al., *Blood* 85:2017–2024 (1995)).

This indicates that these proteins have an established, proven history as therapeutic targets. Clearly there is a need for identification and characterization of further related proteins which can play a role in preventing, ameliorating or correcting dysfunctions or diseases, including, but not limited to, AIDS and neoplastic disorders, among others.

SUMMARY OF THE INVENTION

In one aspect, the invention relates to ELL2 polypeptides and recombinant materials and methods for their production. Another aspect of the invention relates to methods for using such ELL2 polypeptides and polynucleotides. Such uses includes the treatment of neoplastic disorders, among others. In still another aspect, the invention relates to methods to identify agonists and antagonists using the materials provided by the invention, and treating conditions associated with ELL2 imbalance with the identified compounds. Yet another aspect of the invention relates to diagnostic assays for the detection of diseases associated with inappropriate ELL2 activity or levels and mutations in ELL2 that might lead to neoplastic disorders (particularly leukemias).

BRIEF DESCRIPTION OF THE FIGURES

FIGS. 1A–1C shows the nucleotide and deduced amino acid sequence of human ELL2 (SEQ ID NOS:1 and 2, respectively).

FIG. 2 shows a comparison of the deduced amino acid sequences of human ELL2 (SEQ ID NO:2) and ELL (SEQ ID NO:7). Similar amino acids (A,S,T,P; D,E,N,Q; H,R,K; I,L,M,V; F,Y,W) and identical amino acids are boxed.

DETAILED DESCRIPTION OF THE PREFERRED EMBODIMENTS

Definitions

Figure 3:
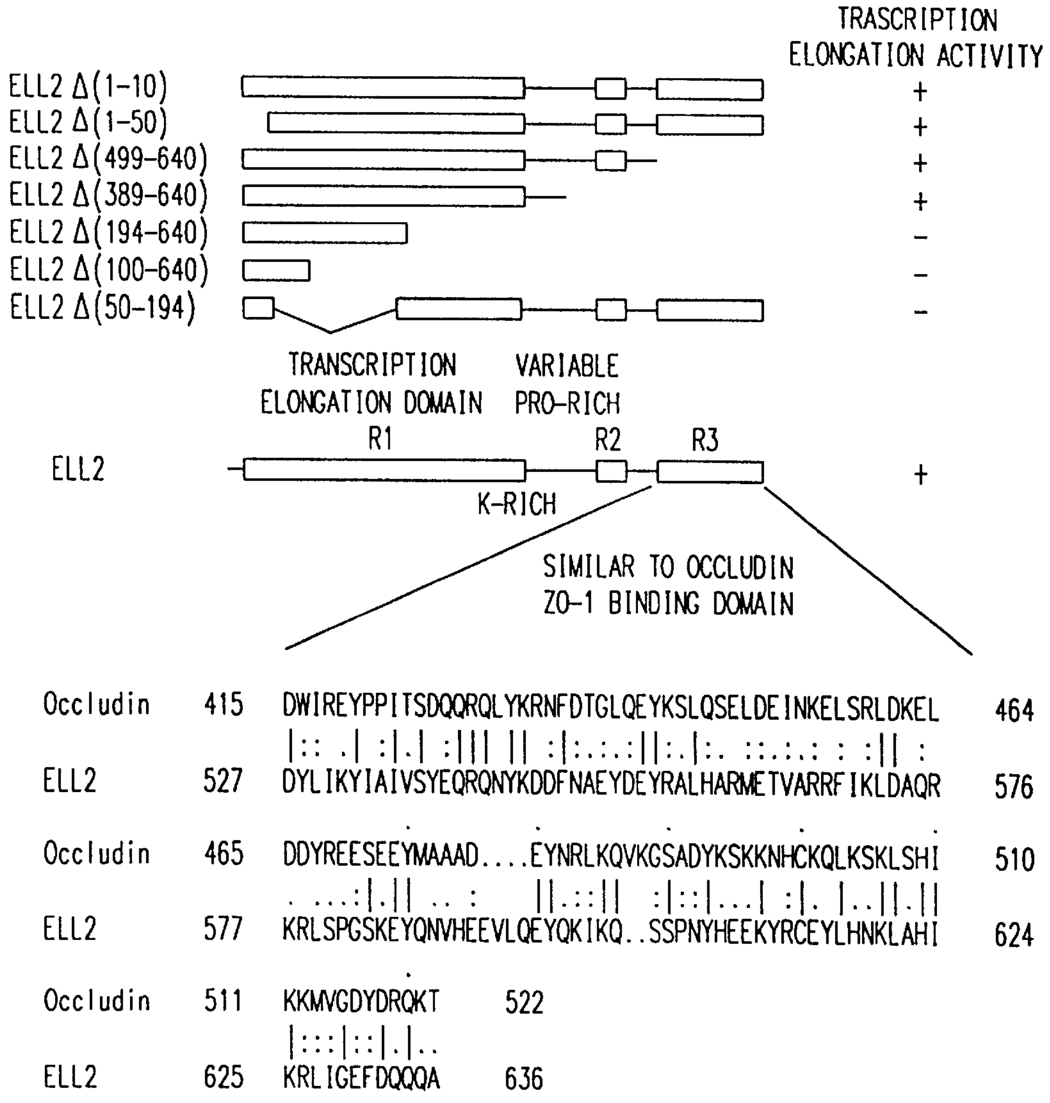
FIG. 3 shows the localization of the ELL2 elongation activation domain and a summary of ELL2 mutants and their activities in transcription. Wild type ELL2 is diagramed at the bottom of the panel. Conserved regions 1, 2, and 3 (R1, R2, and R3) are indicated by the shaded boxes. The alignment of region 3 SEQ ID NO:2 with the C-terminal ZO-1 binding domain of occludin (SEQ ID NO:8) was generated with the BESTFIT program of the Genetics Computer Group package, using the symbol comparison table of Gribskov and Burgess (Gribskov, M. & Burgess, R. R., *Nucleic. Acids. Res.* 14:6745–6763 (1986)).

The following definitions are provided to facilitate understanding of certain terms used frequently herein.

"Neoplastic disorder" refers to a disease state which is related to the hyperproliferation of cells. Neoplastic disorders include, but are not limited to, carcinomas, sarcomas and leukemias.

"Protein Activity" or "Biological Activity of the Protein" refers to the metabolic or physiologic function of said ELL2 protein including similar activities or improved activities or these activities with decreased undesirable side-effects. Also included are antigenic and immunogenic activities of said ELL2 protein. Among the physiological or metabolic activities of said protein are the regulation of the activity of the RNA polymerase II elongation complex. As demonstrated in Example 1, ELL2 increases the overall rate of elongation by RNA polymerase II during both promoter-dependent and -independent transcription. Additional activities include the ability to bind components of the RNA polymerase II elongation complex and SH3 domains.

"ELL2 polypeptides" refers to polypeptides with amino acid sequences sufficiently similar to ELL2 protein sequences that they exhibit at least one biological activity of the protein.

"ELL2 gene" refers to a polynucleotide having the nucleotide sequence set forth in SEQ ID NO:1 or the nucleotide sequence encoding the protein as contained in the cDNA insert of ATCC Deposit No. 97863 or allelic variants thereof and/or their complements.

"ELL2 polynucleotides" refers to a polynucleotide containing a nucleotide sequence which encodes an ELL2 polypeptide or fragment thereof or that encodes an ELL2 polypeptide or fragment wherein said nucleotide sequence has at least 95% identity to a nucleotide sequence encoding the polypeptide of SEQ ID NO:2 or the corresponding fragment thereof or which has sufficient identity to a nucleotide sequence contained in SEQ ID NO:1 or contained in the cDNA insert of ATCC Deposit No. 97863 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of the ELL2 polypeptide can be substantially purified by the one-step method described in Smith and Johnson, *Gene* 67:31–40 (1988).

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications have been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i. e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Methods in Enzymol.* 182:626–646 (1990) and Rattan et al., "Protein Synthesis: Posttranslational Modifications and Aging", *Ann NY Acad Sci* 663:48–62 (1992).

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. (See, e.g.: COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G ., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Preferred computer program methods to determine identity and similarity between two sequences include, but are not limited to, GCS program package (Devereux, J., et al., *Nucleic Acids Research* 12(i):387 (1984)), BLASTP, BLASTN, FASTA (Atschul, S. F., et al., *J Molec Biol* 215:403 (1990)).

By a polynucleotide having a nucleotide sequence at least, for example, 95% "identical" to a reference nucleotide sequence encoding a ELL2 polypeptide is intended that the nucleotide sequence of the polynucleotide is identical to the reference sequence except that the polynucleotide sequence may include up to five point mutations per each 100 nucleotides of the reference nucleotide sequence encoding the ELL2 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Deposited Material

The invention relates to polypeptides and polynucleotides of a novel ELL2 protein, which is related by amino acid sequence identity to the members of the ELL family of RNA polymerase II elongation factors. The invention relates especially to ELL2 materials having the nucleotide and amino acid sequences set out in SEQ ID NOS:1 and 2, and to the ELL2 nucleotide sequences of the human cDNA in ATCC Deposit No. 97863 and amino acid sequence encoded therein.

A deposit containing a human ELL2 cDNA has been deposited with the American Type Culture Collection, 10801 University Blvd., Manassas, Va. 20110-2209, USA, on Jan. 31, 1997, and assigned ATCC Deposit No. 97863. The deposited material is an expression vector referred to as pET-ELL2. This vector was constructed, as described in Example 1, by the insertion of an ELL2 cDNA sequence into the SalI and BamHI sites of M13mpET (Tan, S. et al., *BioTechniques* 16:824–828 (1994)) followed by oligonucleotide-directed mutagenesis (Kunkel, T. A., *Proc. Natl. Acad. Sci. U.S.A.* 82:488–492 (1985)). While the ATCC deposit is believed to contain the ELL2 cDNA sequence shown in SEQ ID NO:1, the nucleotide sequence of the polynucleotide contained in the deposited material, as well as the amino acid sequence of the polypeptide encoded thereby, are controlling in the event of any conflict with any description of sequences herein.

The deposit has been made under the terms of the Budapest Treaty on the international recognition of the deposit of micro-organisms for purposes of patent procedure. The deposit is provided merely as convenience to those of skill in the art and is not an admission that a deposit is required for enablement, such as that required under 35 U.S.C. § 112.

Polypeptides of the Invention

The ELL2 polypeptides of the present invention include the polypeptide of SEQ ID NO:2, as well as polypeptides and fragments which have activity which have at least 90% identity to the polypeptide of SEQ ID NO:2 or the relevant portion and more preferably at least 95%, 97% or 98% identity to the polypeptide of SEQ ID NO:2 and still more preferably at least 99% identity to the polypeptide of SEQ ID NO:2.

The polypeptides of the present invention are preferably provided in an isolated form.

The polypeptides of the present invention include the polypeptide encoded by the deposited cDNA; a polypeptide comprising amino acids from about 1 to about 640 in SEQ ID NO:2; a polypeptide comprising amino acids from about 2 to about 640 in SEQ ID NO:2; a polypeptide comprising amino acids from about 7 to about 350 in SEQ ID NO:2; a polypeptide comprising amino acids from about 50 to about 389 in SEQ ID NO:2; a polypeptide comprising amino acids from about 443 to about 474 in SEQ ID NO:2; a polypeptide comprising amino acids from about 516 to about 640 in SEQ ID NO:2; as well as polypeptides which are at least 95% identical, and more preferably at least 96%, 97%, 98% or 99% identical to the polypeptides described above and also include portions of such polypeptides with at least 30 amino acids and more preferably at least 50 amino acids.

The ELL2 polypeptides may be a part of a larger protein such as a fusion protein. It is often advantageous to include additional amino acid sequence which contains secretory or leader sequences, pro-sequences, sequences which aid in purification such as multiple histidine residues, or additional sequence for stability during recombinant production.

Biologically active fragments of the ELL2 polypeptides are also included in the invention. A fragment is a polypeptide having an amino acid sequence that entirely is the same as part but not all of the amino acid sequence of the aforementioned ELL2 polypeptides. As with ELL2 polypeptides, fragments may be "free-standing," or comprised within a larger polypeptide of which they form a part or region, most preferably as a single continuous region. Representative examples of polypeptide fragments of the invention include, for example, fragments from about amino acid number 1–20, 21–40, 41–60, 61–80, 81–100, 101–120, 121–140, 141–160, 161–180, 181–200, 201–220, 221–240, 241–260, 261–280, 281–300, 301–320, 321–340, 341–360, 361–380, 381–400, 401–420, 421–440, 441–460, 461–480, 481–500, 501–520, 521–540, 541–560, 561–580, 581–600, 601–620, and 621–640. In this context "about" includes the particularly recited ranges larger or smaller by several, a few, 5, 4, 3, 2 or 1 amino acid at either extreme or at both extremes.

Preferred fragments include, for example, truncation polypeptides having the amino acid sequence of ELL2 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate protein activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least 95% identical to that of SEQ ID NO:2 or fragments thereof with at least 95% identity to the corresponding fragment of SEQ ID NO:2 all of which retain the biological activity of the ELL2 protein, including antigenic activity. Included in this group are variants of the defined sequence and fragment. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg, or aromatic residues Phe and Tyr. Particularly preferred are variants in which several, 5–10, 1–5, or 1–2 amino acids are substituted, deleted, or added in any combination.

The ELL2 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the ELL2 polypeptides and polynucleotides closely related thereto.

ELL2 protein of the invention, is structurally related to other proteins of ELL family of RNA polymerase II elongation factors, as shown by the results of sequencing the cDNA encoding human ELL2 in the deposited clone. The cDNA sequence contains an open reading frame encoding a protein of 640 amino acids with a deduced molecular weight of about 72,354 Da. Thus, ELL2 has a molecular weight of about 72 kilodaltons. ELL2 of SEQ ID NO:2 has about 49% identity over its entirety with ELL.

One polynucleotide of the present invention encoding ELL2 protein may be obtained using standard cloning and screening, from a cDNA library derived from mRNA in cells of human fetal heart using the expressed sequence tag (EST) analysis (Adams, M. D., et al., *Science* 252:1651–1656 (1991); Adams, M. D., et al., *Nature* 355:632–634; Adams, M. D., et al., *Nature* 377 Supp:3–174 (1995)). Polynucleotides of the invention can also be obtained from natural sources such as genomic DNA libraries or can be synthesized using well known and commercially available techniques.

Thus, the nucleotide sequence encoding ELL2 polypeptides may be identical over its entire length to the coding sequence in SEQ ID NO:1 or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least 95% identical, with a nucleotide sequence encoding an ELL2 polypeptide or at least 95% identical with the encoding nucleotide sequence set forth in SEQ ID NO:1.

When the polynucleotides of the invention are used for the recombinant production of ELL2 polypeptide, the polynucleotide may include the coding sequence for the full-length polypeptide or a fragment thereof, by itself; the coding sequence for the full-length polypeptide or fragment in reading frame with other coding sequences, such as those encoding a leader or secretory sequence, a pre-, or pro or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* 86:821–824 (1989), or is an HA tag. The polynucleotide may also contain non-coding 5' and 3' sequences, such as transcribed, non-translated sequences, splicing and polyadenylation signals, ribosome binding sites and sequences that stabilize mRNA.

Among particularly preferred embodiments of the invention are polynucleotides encoding ELL2 polypeptides having the amino acid sequence of set out in SEQ ID NO:2 and variants thereof.

Embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO:2, but lacking the N-terminal methionine; (c) a nucleotide sequence encoding the polypeptide having the amino acid sequence at positions from about 7 to about 350 in SEQ ID NO:2; (d) a nucleotide sequence encoding the polypeptide having the amino acid sequence at positions from about 50 to about 389 in SEQ ID NO:2; (e) a nucleotide sequence encoding the polypeptide having the amino acid sequence at positions from about 443 to about 474 in SEQ ID NO:2; (f) a nucleotide sequence encoding the polypeptide having the amino acid sequence at positions from about 516 to about 640 in SEQ ID NO:2; (g) a nucleotide sequence encoding the polypeptide having the amino acid sequence encoded by the cDNA clone contained in ATCC Deposit No. 97863; or (h) a nucleotide sequence complementary to any of the nucleotide sequences in (a), (b), (c), (d), (e), (f), or (g).

As a practical matter, whether any particular nucleic acid molecule is at least 95%, 96%, 97%, 98% or 99% identical to, for instance, the nucleotide sequence shown in SEQ ID NO:1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711).

Further preferred embodiments are polynucleotides encoding ELL2, ELL2 variants that have the amino acid sequence of the ELL2 protein of SEQ ID NO:2 in which several, 5–10, 1–5, 1–3, 1–2 or 1 amino acid residues are substituted, deleted or added, in any combination.

Further preferred embodiments of the invention are polynucleotides that are at least 95% identical over their entire length to a polynucleotide encoding the ELL2 polypeptide having the amino acid sequence set out in SEQ ID NO:2, and polynucleotides which are complementary to such polynucleotides. Most highly preferred are polynucleotides that comprise a region that is at least 95% identical over their entire length to a polynucleotide encoding the ELL2 polypeptide of the human cDNA of the deposited clone and polynucleotides complementary thereto. In this regard, polynucleotides at least 96% identical over their entire length to the same are particularly preferred, and those with at least 97% are especially preferred. Furthermore, those with at least 98% are highly preferred and with at least 99% being the most preferred.

In addition, the present inventors have identified the following cDNAs related to extensive portions of SEQ ID NO:1: HPRAE28R (SEQ ID NO:9), HSBAI43R (SEQ ID NO:10), HNEAK22RA (SEQ ID NO:11), HPRTS01R (SEQ ID NO:12), HBWAL95R (SEQ ID NO:13), and HSXCR53RA (SEQ ID NO:14). In one specific embodiment, the nucleic acid molecules of the invention are not the cDNAs identified in any of SEQ ID NO:9, SEQ ID NO:10, SEQ ID NO:11, SEQ ID NO:12, SEQ ID NO:13, and SEQ ID NO:14.

The following public ESTs, which relate to portions of SEQ ID NO:1, have also been identified: W92650 (SEQ ID NO:15), W94585 (SEQ ID NO:16), AA243384 (SEQ ID NO:17), AA655966 (SEQ ID NO:18), N39822 (SEQ ID NO:19), AA545429 (SEQ ID NO:20), R16400 (SEQ ID NO:21), T89063 (SEQ ID NO:22), AA370048 (SEQ ID NO:23), AA375277 (SEQ ID NO:24), R12663 (SEQ ID NO:25), AA414990 (SEQ ID NO:26), AA252607 (SEQ ID NO:27), AA191245 (SEQ ID NO:28), AA524290 (SEQ ID NO:29), AA370180 (SEQ ID NO:30), Z20670 (SEQ ID NO:31), and AA009921 (SEQ ID NO:32).

The present invention is further directed to fragments of the isolated nucleic acid molecules described herein. By a fragment of an isolated nucleic acid molecule having the nucleotide sequence of the deposited cDNA or the nucleotide sequence shown in SEQ ID NO:1 is intended fragments at least about 15 nt, and more preferably at least about 20 nt, still more preferably at least about 30 nt, and even more preferably, at least about 40 nt in length which are useful as diagnostic probes and primers as discussed herein. Of course larger DNA fragments 50, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, or 2139 nt in length of the sequence shown in SEQ ID NO:1 are also useful according to the present invention as are fragments corresponding to most, if not all, of the nucleotide sequence of the cDNA clone contained in the plasmid deposited as ATCC Deposit No. 97863 or as shown in SEQ ID NO:1. By a fragment at least 20 nt in length, for example, is intended fragments which include 20 or more contiguous bases from the nucleotide sequence of the deposited cDNA or the nucleotide sequence as shown in SEQ ID NO:1.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention which are sufficiently identical to a nucleotide sequence contained in SEQ ID NO:1 or in the cDNA insert of ATCC Deposit No. 97863, may be used as hybridization probes for cDNA and genomic DNA, to isolate full-length cDNAs and genomic clones encoding ELL2 protein and to isolate cDNA and genomic clones of other genes that have a high sequence similarity to the ELL2 gene. Such hybridization techniques are known to those of skill in the art. Typically, these nucleotide sequences are 95% identical, preferably 96% identical, more preferably 97%, 98% or 99% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In a more specific embodiment, the nucleic acid molecules of the present invention, e.g., isolated nucleic acids comprising a polynucleotide having a nucleotide sequence encoding an ELL2 polypeptide or fragments thereof, are not the sequence of nucleotides, the nucleic acid molecules (e.g., clones), or the nucleic acid inserts identified in one or more of the following GenBank Accession Reports: W92650, W94585, AA243384, AA655966, N39822, AA545429 R16400, T89063, AA370048, AA375277, R12663, AA414990, AA252607, AA191245, AA524290, AA370180, Z20670, and AA009921, all of which are incorporated herein by reference.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and the production of polypeptides of the invention by recombinant techniques. Cell-free translation systems can also be employed to produce such proteins using RNAs derived from the DNA constructs of present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment appropriate secretion signals may be incorporated into the desired polypeptide. These signals may be endogenous to the polypeptide or they may be heterologous signals.

As used herein, the term "operably linked," when used in the context of a linkage between a structural gene and an expression control sequence, e.g., a promoter, refers to the position and orientation of the expression control sequence relative to the structural gene so as to permit expression of the structural gene in any host cell. For example, an operable linkage would maintain proper reading frame and would not introduce any in frame stop codons.

As used herein, the term "heterologous promoter," refers to a promoter not normally and naturally associated with the structural gene to be expressed. For example, in the context of expression of an ELL2 polypeptide, a heterologous promoter would be any promoter other than an endogenous promoter associated with the ELL2 gene in non-recombinant human chromosomes. In specific embodiments of this invention, the heterologous promoter is not a prokaryotic or bacteriophage promoter, such as the lac promoter, T3 promoter, or T7 promoter. In other embodiments, the heterologous promoter is a eukaryotic promoter.

In other embodiments this invention provides an isolated nucleic acid molecule comprising an ELL2 structural gene operably linked to a heterologous promoter. As used herein, the term "an ELL2 structural gene" refers to a nucleotide sequence at least 95% identical to one of the following nucleotide sequences:

(a) a nucleotide sequence encoding the ELL2 polypeptide having the complete amino acid sequence in SEQ ID NO:2;

(b) a nucleotide sequence encoding the ELL2 polypeptide having the amino acid sequence at positions 2–640 in SEQ ID NO:2;

(c) a nucleotide sequence encoding the ELL2 polypeptide having the complete amino acid sequence encoded by the cDNA clone contained in ATCC Deposit No. 97863; or (d) a nucleotide sequence complementary to any of the nucleotide sequences in (a), (b), or (c).

In more preferred embodiments, the ELL2 structural gene is 96%, 97%, 98%, 99%, or 100% identical to one or more of nucleotide sequences (a), (b), or (c) supra.

This invention also provides an isolated nucleic acid molecule comprising an ELL2 structural gene operably linked to a heterologous promoter, wherein said isolated nucleic acid molecule does not encode a fusion protein comprising the ELL2 structural gene or a fragment thereof. In particular embodiments the isolated nucleic acid molecule does not encode a beta-galactosidase-ELL2 fusion protein.

This invention further provides an isolated nucleic acid molecule comprising an ELL2 structural gene operably linked to a heterologous promoter, wherein said isolated nucleic acid molecule is capable of expressing an ELL2 polypeptide when used to transform an appropriate host cell. In particular embodiments, the ELL2 polypeptide does not contain and is not covalently linked to an amino acid sequence encoded by the 5' untranslated portion of the ELL2 gene, e.g., nucleotides 1–93 of SEQ ID NO:1, or a fragment thereof.

This invention also provides an isolated nucleic acid molecule comprising a polynucleotide having a nucleotide sequence at least 95% identical to a sequence encoding a ELL2 polypeptide having the amino acid sequence of SEQ ID NO:2, wherein said isolated nucleic acid molecule does not contain a nucleotide sequence at least 90% identical to the 3' untranslated region of SEQ ID NO:1 (nucleotides 2014–2139), or a fragment of the 3' untranslated region greater than 25, 50, 75, 100, or 125 bp in length. In other embodiments, said isolated nucleic acid molecule does not contain a nucleotide sequence at least 91%, 92%, 93%, 94%, 95%, 96%, 97%, 98%, 99%, or 100% identical to the 3' untranslated region of SEQ ID NO:1 (nucleotides 2014–2139).

This invention further provides an isolated nucleic acid molecule comprising a polynucleotide having a nucleotide sequence at least 95% identical to a sequence encoding a ELL2 polypeptide having the amino acid sequence of SEQ ID NO:2, wherein said isolated nucleic acid molecule does not contain a nucleotide sequence at least 90% identical to the 5' untranslated region of SEQ ID NO:1 (nucleotides 1–93), or a fragment of the 5' untranslated region greater than 25, 35, 45, 55, 65, 75, 85, or 90 bp. In other embodiments, said isolated nucleic acid molecule does not contain a nucleotide sequence at least 91%, 92%, 93%, 94%, 95%, 96%, 97%, 98%, 99%, or 100% identical to the 5' untranslated region of SEQ ID NO:1 (nucleotides 1–93).

In addition, the present invention further includes novel expression vectors comprising operator and promoter elements operatively linked to nucleotide sequences encoding a protein of interest. One example of such a vector is pHE4-5 which is described in detail below.

Figure 4:
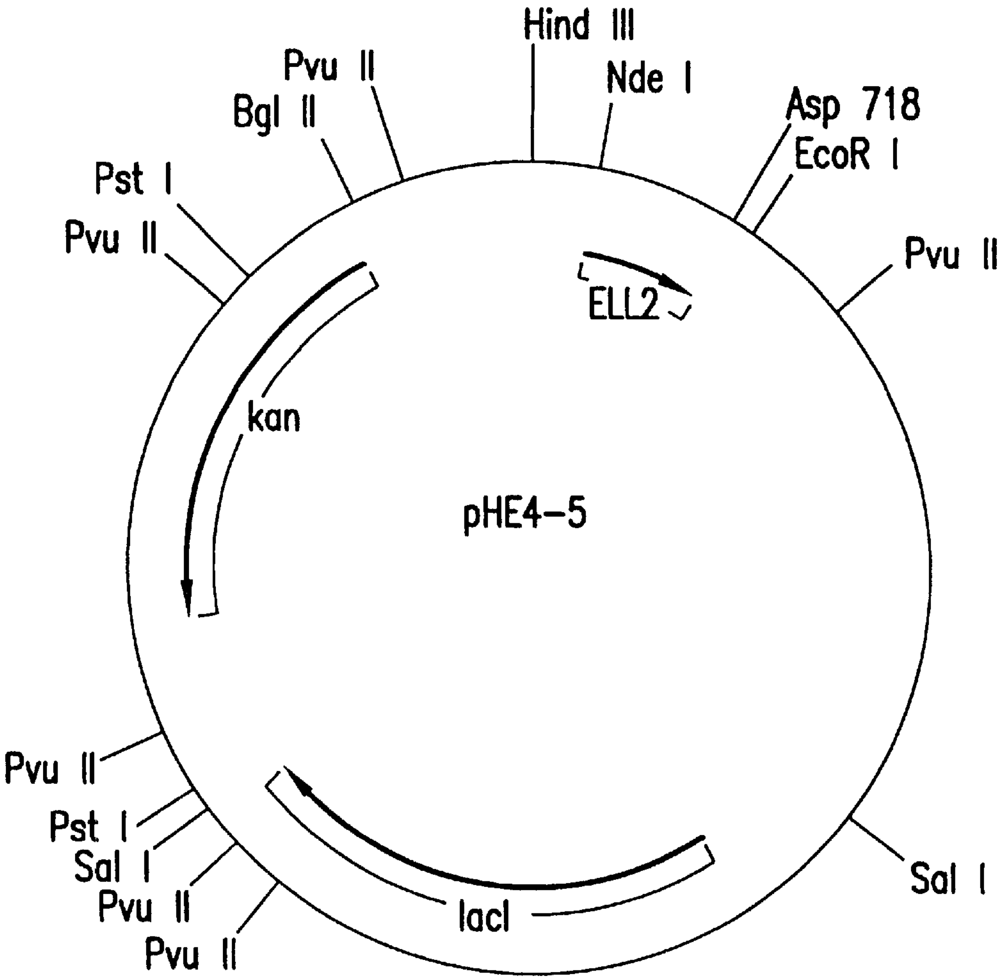
FIG. 4 shows a schematic representation of the pHE4-5 expression vector (SEQ ID NO:33) and the subcloned ELL2 cDNA coding sequence. The locations of the kanamycin resistance marker gene, the ELL2 coding sequence, the oriC sequence, and the lacIq coding sequence are indicated.
Figure 5:
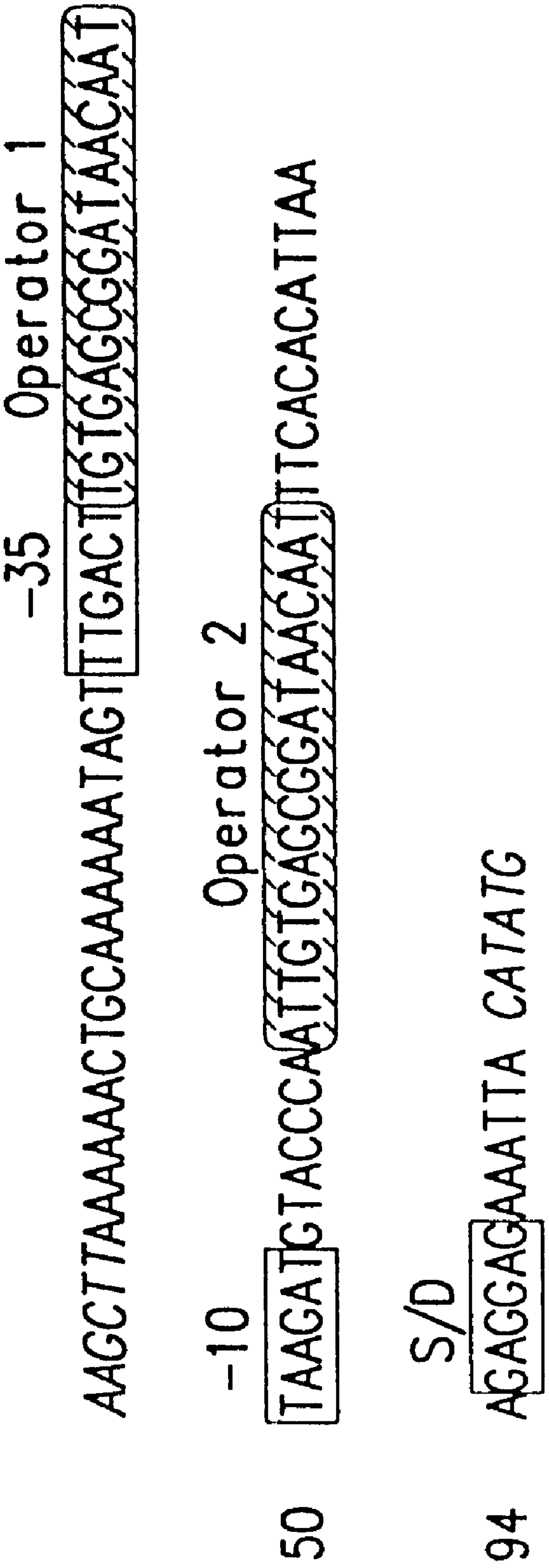
FIG. 5 shows the nucleotide sequence of the regulatory elements of the pHE promoter (SEQ ID NO:34). The two lac operator sequences, the Shine-Delgamo sequence (S/D), and the terminal HindIII and NdeI restriction sites (italicized) are indicated.

As summarized in FIG. 4 and FIG. 5, components of the pHE4-5 vector (SEQ ID NO:33) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. A nucleotide sequence encoding ELL2 (SEQ ID NO:1), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of downstream (i. e., 3') sequences. However, the lacIq gene product dissociates from the lac operator in the presence of either lactose or certain lactose analogs, e.g., isopropyl B-D-thiogalactopyranoside (IPTG). ELL2 thus is not produced in appreciable quantities in uninduced host cells containing the pHE4-5 vector. Induction of these host cells by the addition of an agent such as IPTG, however, results in the expression of the ELL2 coding sequence.

The promoter/operator sequences of the pHE4-5 vector (SEQ ID NO:33) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4-5 vector except for the ELL2 coding sequence. Features of the pHE4 vectors include optimized synthetic T5 phage promoter, lac operator, and Shine-Delgamo sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:33).

If the ELL2 polypeptide is to be expressed for use in screening assays, generally, it is preferred that the polypeptide be produced at the surface of the cell. In this event, the cells may be harvested prior to use in the screening assay. If ELL2 polypeptide is secreted into the medium, the medium can be recovered in order to recover and purify the polypeptide; if produced intracellularly, the cells must first be lysed before the polypeptide is recovered.

ELL2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performnance liquid chromatography is employed for purification. Well known techniques for refolding proteins may be employed to regenerate active conformation when the polypeptide is denatured during isolation and or purification.

Diagnostic Assays

This invention also relates to the use of ELL2 polynucleotides for use as diagnostic reagents. Detection of a mutated form of ELL2 gene associated with a dysfunction will provide a diagnostic tool that can add to or define a diagnosis of a disease or susceptibility to a disease which results from under-expression, over-expression or altered expression of ELL2. Individuals carrying mutations in the ELL2 gene may be detected at the DNA level by a variety of techniques. Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled ELL2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* 230:1242 (1985). Sequence changes at specific locations may also be revealed by nuclease protection assays, such as RNase and S1 protection or the chemical cleavage method. See Cotton et al., *Proc. Natl. Acad. Sci. USA* 85:4397–4401 (1985).

The diagnostic assays offer a process for diagnosing or determining a susceptibility to neoplastic disorders through detection of mutation in the ELL2 gene by the methods described.

In addition, neoplastic disorders, can be diagnosed by methods comprising determining from a sample derived from a subject an abnormally decreased or increased level of ELL2 polypeptide or ELL2 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an ELL2 protein, in a sample derived from a host are well-known to those of skill in the art. Such assay methods include radioimmunoassays, competitive-binding assays, Western Blot analysis and ELISA assays.

Additionally, methods are provided for diagnosing or determining a susceptibility of an individual to neoplastic disorders, comprising (a) assaying ELL2 protein gene expression level in mammalian cells or body fluid; and (b) comparing said ELL2 protein gene expression level with a standard ELL2 protein gene expression level whereby an increase or decrease in said ELL2 gene expression level over said standard is indicative of an increased or decreased susceptibility to a neoplastic disorder.

Chromosome Assays

The nucleotide sequences of the present invention are also valuable for chromosome identification. The sequence is specifically targeted to and can hybridize with a particular location on an individual human chromosome. For example, ELL2 sequences have been found by fluorescent in situ hybridization to bind to human chromosomes at 1 q21 and 5 q15. The inventors have further found that the hybridization signal from the 1 q21 locus is significantly stronger than that at 5 q15.

The mapping of relevant sequences to chromosomes according to the present invention is an important first step in correlating those sequences with genes associated disease. Once a sequence has been mapped to a precise chromosome location, the physical position of the sequence on the chromosome can be correlated with genetic map data. Such data are found, for example, in V. McKusick, Mendelian Inheritance in Man (available on-line through Johns Hopkins, University Welch Medical Library). The relationship between genes and diseases that have been mapped to the same chromosomal region are then identified through linkage analysis (coinheritence of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the ELL2 Polypeptides. By "immunospecific" is meant that the antibodies have affinities for the polypeptides of the invention that are substantially greater in their affinities for related polypeptides such as the analogous proteins of the prior art.

Antibodies generated against the ELL2 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* 256:495–497 (1975)), the trioma technique, the human B-cell hybridoma technique (Kozbor et al., *Immunology Today* 4:72 (1983)) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against ELL2 polypeptides may also be employed to treat neoplastic disorders, among others.

Screening Assays

The ELL2 of the present invention may be employed in a screening process for compounds which bind the protein and which activate (agonists) or inhibit activation of (antagonists) the polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1 (2):Chapter 5 (1991).

By "agonist" is intended naturally occurring and synthetic compounds capable ofenhancing an ELL2 activity (e.g., promoting ELL2 catalyzed increased rate of RNA elongation during transcription). By "antagonist" is intended naturally occurring and synthetic compounds capable of inhibiting an ELL2 activity.

ELL2 proteins are associated with many pathologies. Accordingly, it is desirous to find compounds and drugs which stimulate ELL2 on the one hand and which can inhibit the function of ELL2 on the other hand. In general, agonists are employed for therapeutic and prophylactic purposes including the treatment of ceratin types of neoplastic disorders. For example, the ELL gene was originally isolated as a gene that undergoes frequent translocations in acute myeloid leukemia (Thirman, M. J. et al., *Proc. Natl. Acad. Sci. U.S.A*. 91:12110–12114 (1994), Mitani, K. et al., *Blood* 85:2017–2024 (1995)). ELL2 gene translocations could result in similar disorders which may be treated by enhancing ELL2 activity, e.g., by administration of an ELL2 agonist or an ELL2 polypeptide. Further, overexpression of ELL leads to the transformation of fibroblasts. Thus, antagonists of ELL2 activity may be employed for a variety of therapeutic and prophylactic purposes including the treatment of certain types of neoplastic disorders associated with overexpression of ELL2.

In general, such screening procedures involve producing appropriate cells which express the polypeptide of the present invention on the surface thereof. Such cells include cells from mammals, yeast, Drosophila or *E. coli*. Cells expressing the protein (or cell membrane containing the expressed protein) are then contacted with a test compound to observe binding, or stimulation or inhibition of a functional response.

The assays may simply test binding of a candidate compound wherein adherence to the cells bearing the protein is detected by means of a label directly or indirectly associated with the candidate compound or in an assay involving competition with a labeled competitor. Further, these assays may test whether the candidate compound results in a signal generated by activation of the protein, using detection systems appropriate to the cells bearing the protein at their surfaces. Inhibitors of activation are generally assayed in the presence of a known agonist and the effect on activation by the agonist by the presence of the candidate compound is observed. Standard methods for conducting such screening assays are well understood in the art.

Examples of potential ELL2 protein antagonists include antibodies or, in some cases, oligonucleotides or proteins which are closely related to the ligands of the ELL2 protein, e.g., a fragment of the ligand, or small molecules which bind to the protein but do not elicit a response, so that the activity of the protein is prevented. Such ligands include other molecules involved in the process of transcription and SH3 domains.

Prophylactic and Therapeutic Methods

This invention provides methods of treating an abnormal conditions related to both an excess of and insufficient amounts of ELL2 protein activity.

If the activity of ELL2 protein is in excess, several approaches are available. One approach comprises administering to a subject an inhibitor compound (antagonist) as hereinabove described along with a pharmaceutically acceptable carrier in an amount effective to inhibit activation by blocking binding of ligands to the ELL2 protein, or by inhibiting a second signal, and thereby alleviating the abnormal condition.

In another approach, soluble forms of ELL2 polypeptides still capable of binding the ligand in competition with endogenous ELL2 protein may be administered. Typical embodiments of such competitors comprise fragments of the ELL2 polypeptide.

In still another approach, expression of the gene encoding endogenous ELL2 protein can be inhibited using expression blocking techniques. Known such techniques involve the use of antisense sequences, either internally generated or separately administered. See, for example, O'Connor, J. Neurochem 56:560 (1991) in OLIGODEOXYNUCLEOTIDES AS ANTISENSE INHIBITORS OF GENE EXPRESSION, CRC Press, BocaRaton, Fla. (1988). Alternatively, oligonucleotides which form triple helices with the gene can be supplied. See, for example, Lee et al., *Nucleic Acids Res* 6:3073 (1979); Cooney et al., *Science* 241:456 (1988); Dervan et al., *Science* 251:13 60 (1991). These oligomers can be administered per se or the relevant oligomers can be expressed in vivo.

For treating abnormal conditions related to an under-expression of ELL2 and its activity, several approaches are also available. One approach comprises administering to a subject a therapeutically effective amount of a compound which activates ELL2, i.e., an agonist as described above, in combination with a pharmaceutically acceptable carrier, to thereby alleviate the abnormal condition. Alternatively, gene therapy may be employed to effect the endogenous production of ELL2 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Strachan, T. & Read A. P., Chapter 20, "Gene Therapy and Other Molecular Genetic-based Therapeutic Approaches," (and references cited therein) in HUMAN MOLECULAR GENETICS, BIOS Scientific Publishers Ltd. (1996).

Formulation and Administration

Peptides, such as the soluble form of ELL2 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLE

The example below is carried out using standard techniques, which are well known and routine to those of skill in the art, except where otherwise described in detail. The example illustrates, but does not limit the invention.

Example 1

Material and Methods

Cloning and Expression of Wild Type and Mutant ELL2

A DNA fragment including ELL2 coding sequences was obtained by PCR amplification of a Lambda Zap human fetal heart library (Stratagene) using a 5' primer (5'-CAATTAACCCTCATAAAGGGAAC-3') (SEQ ID NO:3) identical to a sequence in the Lambda Zap vector and a 3' antisense primer (5'-CAAAGTTTCACCTTTTAGAATC-TAGAGCAACTC-3') (SEQ ID NO:4) corresponding to a sequence in the 3'-untranslated region of the ELL2 gene. The construct for expression of histidine-tagged ELL2 in bacteria was prepared in two steps. First, a DNA fragment encoding ELL2 amino acids 11–640 was generated by PCR amplification of the original ELL2 ORF-containing PCR product using the ELL2- specific primers:
5'-GAGGTGTCGACGAGGAGCAGCGCTATGGGCTGT-CGTGCGGAC-3' (SEQ ID NO:5) and
5'-GTGTGGATCCTCATCACTAGGACCATGACTCTGC-TTGCTGTTG-3' (SEQ ID NO:6) and was introduced into the SalI and BamHI sites of M13mpET (Tan, S. et al., *BioTechniques* 16:824–828 (1994)). An expression vector containing the entire ELL2 ORF was then generated by oligonucleotide-directed mutagenesis (Kunkel, T. A., *Proc. Natl. Acad. Sci. U.S.A.* 82:488–492 (1985)) with the Muta-Gene Ml 3 in vitro mutagenesis kit (Bio-Rad) and confirmed by DNA sequencing; N- and C-terminal ELL2 deletion mutants were constructed by the same procedure. Wild type and mutant ELL2 proteins were expressed in *E. coli*, purified from guanidine-solubilized inclusion bodies by nickel affinity chromatography, and renatured as described by Shilatifard, A. et al., *Science* 271:1873–1876 (1996). Where indicated, the ELL2 protein was further purified by preparative SDS-polyacrylamide gel electrophoresis (Shilatifard, A. et al., *Science* 271:1873–1876 (1996)). The human ELL protein was expressed in *E. coli* and purified as described (Shilatifard, A. et al., *Science* 271:1873–1876 (1996)).

Tissue distribution of ELL2 and ELL mRNAs

A human multiple tissue northern blot (MTN1, Clontech) was probed with PCR generated, ELL2- and ELL-specific probes chosen from a region of sequence that was most divergent between the two genes. The ELL-specific probe contained sequences encoding amino acids 317–621, and the ELL2-specific probe contained sequences encoding amino acids 327–474. Probes were labeled with [α-$^{32}$P]dCTP by random priming performed according to the manufacturer's instructions (Rediprime kit, Amersham). The blot was pre-hybridized in 10 ml of Hybrisol I solution (Oncor) for 3 hr at 42° C. Probe DNA was denatured and added to hybridization solution at $10^6$ cpm/ml of solution. Hybridization was carried out at 42° C. overnight. The blot was washed 10 min in 2×SSC/0.1% SDS at room temperature, 15 min in 0.2×SSC/0.1% SDS at 45° C., 10 min in 0.1×SSC/0.1% SDS at 55° C., and then exposed to film (Hyperfilm-MP, Amersham) overnight at −80° C.

Assay of the effects of ELL2 on elongation by RNA polymerase II during synthesis of promoter-independent and promoter-dependent transcripts ELL2 and ELL have similar effects on elongation by RNA polymerase II during synthesis of promoter-independent and promoter-dependent transcripts. 10% SDS-PAGE of recombinant ELL2 (rELL2) and ELL (rELL), purified by nickel chromatography and preparative SDS-PAGE. Proteins were visualized by silver staining. Effects of ELL2 and ELL on the kinetics of promoter-dependent transcription. Preinitiation complexes were assembled at the AdML promoter with recombinant TBP, TFIIB, TFIIE, TFIIF, and purified rat TFIIH and RNA polymerase II as described (Shilatifard, A. et al., *Science* 271:1873–1876 (1996)). Transcription was initiated by addition of 50 μM ATP, 50 μM GTP, 2 μM UTP, 10 μCi of [α-$^{32}$P]CTP (>400 Ci/mmol, Amersham) and 7 mM $MgCl_2$. After 10 min at 28° C., 100 μM nonradioactive CTP was added to reaction mixture and short transcripts were chased in the absence or presence of ~50 ng SDS-PAGE purified rELL2 or rELL for the times indicated. Transcripts were analyzed by electrophoresis through a 6% polyacrylamide, 7.0 M urea gel.

The following procedure was used to determine the effects that ELL2 and ELL have on the kinetics of promoter-independent transcription. SDS/PAGE purified histidine-tagged ELL2 and ELL proteins were renatured and assayed in pulse-chase reactions using the oligo(dC)-tailed template pCpGR220 S/P/X. Reactions contained ~0.01 units of RNA polymerase II, 100 ng of pCpGR220S/P/X, and ~50 ng rELL2 or ~50 ng ELL and were performed essentially as described (Shilatifard, A. et al., *Science* 271:1873–1876 (1996)). The control reaction (mock) contained an identically prepared fraction from uninfected JM109(DE3) cells.

Localization of the ELL2 elongation activation domain

Wild type ELL2 and ELL2 mutants were expressed in *E. coli* and purified by nickel affinity chromatography as described above. Approximately 50 ng of each protein (in a maximum volume of 50 μl) was renatured and assayed as described (Shilatifard, A. et al., *Science* 271:1873–1876 (1996)) for its ability to stimulate synthesis of the 135 nucleotide transcript from the T-less cassette of oligo(dC)-tailed template pCpGR220 S/P/X. Reactions containing ~0.01 unit RNA polymerase II, 100 ng template, and the indicated ELL2 proteins were incubated at 28° C. for 5 min in the presence of 50 μM ATP, 50 μM GTP, 1.8 μM CTP, and 10 μCi [α-$^{32}$P]CTP. The control reaction (mock) contained an identically prepared fraction from uninfected JM109 (DE3) cells.

Results

Identification of Human ELL2

Searches of the Human Genome Sciences and GenBank EST databases identified multiple overlapping ESTs that formed a contig spanning a predicted ELL2 ORF similar in sequence to the ORF of the human ELL gene (FIG. 2). An ~1.9 kb DNA fragment containing the entire predicted ELL2 ORF was obtained by PCR amplification of a human fetal heart library and sequenced. The ELL2 ORF encodes a 640 amino acid protein with a calculated molecular mass of 72,354 Da. As determined by the BESTFIT program of the Genetics Computer Group (GCG, Madison, Wis.) package (Genetics Computer Group, Program Manual for the GCG Package, Version 8 (Madison, Wis.) (1994)), ELL2 is 49% identical and 66% similar to ELL (alignment score ~64 SD).

Expression of ELL2 and ELL in Human Cells

To investigate the expression of ELL2 and ELL in human cells, Northern blots containing poly $A^+$RNA from various human tissues were hybridized with ELL2- and ELL-specific probes. Consistent with previous studies (Thirman, M. J. et al., *Proc. Natl. Acad. Sci. U.S.A.* 91:12110–12114 (1994), Mitani, K. et al., *Blood* 85:2017–2024 (1995)), the ELL-specific probe hybridized to two mRNA species of ~4.4 kb and ~2.7 kb. The ELL2-specific probe hybridized to two mRNA species of ~7 kb and ~4.1 kb. At present, it is not clear whether the ~7 kb and 4.1 kb ELL2 mRNAs are alternatively processed forms or the products of closely related genes. The results of Northern blot analysis indicate that both ELL2 and ELL mRNAs are expressed in many of the same tissues, i.e., both ELL2 and ELL mRNAs are expressed at the highest levels in pancreas, skeletal muscle, placenta, and heart, and at lower levels in lung, and brain. Unlike ELL, ELL2 is expressed at high levels in liver, but at nearly undetectable levels in kidney. Notably, the ratio of ELL2 and ELL mRNAs, as well as the ratios of the two different forms of each mRNA, exhibit tissue to tissue variation.

ELL2 and ELL Possess Similar Transcriptional Activities

ELL is capable of potently stimulating the overall rate of RNA chain elongation by RNA polymerase II (Shilatifard, A. et al., *Science* 271:1873–1876 (1996)). To demonstrate that ELL2 is also capable of stimulating elongation by RNA polymerase II, a DNA fragment containing the ELL2 ORF was introduced into a bacteriophage M13 expression vector under control of the T7 RNA polymerase promoter (Tan, S. et al., *BioTechniques* 16:824–828 (1994)) and expressed in *E. coli* with an N-terminal histidine tag. The recombinant ELL2 protein was purified to homogeneity from guanidine-solubilized inclusion bodies by nickel affinity chromatography and preparative SDS-gel electrophoresis, and tested for its ability to stimulate elongation.

ELL2 is an RNA polymerase II elongation factor with functional properties similar to those of ELL. The abilities of ELL2 and ELL to stimulate elongation were compared during either promoter-specific transcription carried out in the presence of the general initiation factors or promoter-independent transcription carried out using an oligo(dC)-tailed template assay, in the absence of auxiliary transcription factors.

To compare the abilities of ELL2 and ELL to stimulate the rate of elongation of promoter-specific transcripts, preinitiation complexes were assembled by preincubation of purified RNA polymerase II, TBP, TFIIB, TFIIE, TFIIF, and TFIIH with a DNA template containing the AdML promoter. Short, highly radioactive transcripts were then synthesized during a brief pulse carried out in the presence of ATP, GTP, UTP, and a limiting concentration of [α-$^{32}$P]CTP. These short, promoter-specific transcripts were then chased into full-length runoff transcripts in the presence of an excess of nonradioactive CTP and in the presence or absence of approximately equivalent levels of recombinant ELL2 or ELL. Comparison of the kinetics of accumulation of full-length runoff transcripts reveals that ELL2 and ELL have similar effects on the rate of elongation of promoter-specific transcripts by RNA polymerase II.

An oligo(dC)-tailed template assay was used to compare the abilities of ELL2 and ELL to stimulate the rate of elongation of promoter-independent transcripts. Briefly, transcription was initiated by addition of RNA polymerase II to reaction mixtures containing the oligo(dC)-tailed template pCpGR220 S/P/X (Rice, G. A. et al., *Proc. Natl. Acad. Sci. U.S.A.* 88:4245–4249 (1991)), ATP, GTP, and [$\alpha$-$^{32}$P] CTP. Under these conditions, RNA polymerase II synthesizes ~135 nucleotide transcripts on the T-less cassette of pCpGR220 S/P/X. These highly radioactive transcripts were then chased into longer RNAs with UTP and an excess of nonradioactive CTP, in the presence or absence of approximately equivalent levels of recombinant ELL2 or ELL. Transcripts synthesized in the presence of either ELL2 or ELL were substantially longer than transcripts synthesized in their absence; we note that many transcripts synthesized in the presence of ELL2 and ELL appear to be plasmid length. In addition, comparison of the kinetics of accumulation of long transcripts and of the distribution of RNA intermediates reveals that ELL2 and ELL have similar effects on elongation of transcripts synthesized by RNA polymerase II in the absence of auxiliary transcription factors on the oligo(dC)-tailed pCpGR220 S/P/X template.

Localization of the ELL2 Elongation Activation Domain

Comparison of the ELL2 and ELL ORFs revealed three conserved regions (FIG. 2 and FIG. 3): an N-terminal region (region 1) between ELL2 residues 7 and 350, a short lysine-rich region (region 2) between ELL2 residues 443 and 474, and a C-terminal region (region 3) between ELL2 residues 516 and 640. Although neither ELL2 nor ELL have obvious structural features such as zinc finger, leucine zipper, or helix-turn-helix motifs commonly found in transcription factors, a TBLASTN search of the GenBank database revealed that conserved region 3 of ELL2 and ELL exhibits striking similarity to the ZO-1 binding domain of occludin (SEQ ID NO:8) (Furuse, M. et al., *J. Cell. Bio.* 127:1617–1626 (1994)), an integral membrane protein found at tight junctions (Furuse, M. et al., *J. Cell. Bio.* 123:1777–1788 (1993)). As determined by the BESTFIT program of the Genetics Computer Group (GCG, Madison, Wis.) package (Genetics Computer Group, Program Manual for the GCG Package, Version 8 (Madison, Wis.) (1994)), the C-terminus of ELL2 and the ZO-1 binding domain of occludin are 33% identical and 61% similar (alignment score ~17 SD) over a 112 amino acid region. In addition, ELL2 and ELL each contain a proline-rich, non-conserved region that bridges conserved regions 1 and 2. The ELL2 proline-rich region includes several PXXP motifs that are potential binding sites for SH3 domains (Yu, H. et al., *Cell* 76:933–945 (1996)).

To assess the functional significance of the regions conserved between ELL2 and ELL and to localize the ELL2 elongation activation domain, a series of ELL2 deletion mutants was constructed (FIG. 3), expressed in *E. coli* purified, and tested for transcriptional activity using the oligo(dC)-tailed template assay. The results of these experiments localize the ELL2 elongation activation domain to sequences in conserved region 1 between residues 50 and 389. ELL2 deletion mutants Δ194–640, Δ100–640, and Δ50–194, which each lack significant portions of region 1, had significantly reduced transcriptional activities. In contrast, ELL2 deletion mutants Δ1–10, Δ1–50, Δ499–640, and Δ389–640 all exhibited near wild type levels of activity.

Discussion

Here we report identification and characterization of ELL2, a novel RNA polymerase II elongation factor similar to previously characterized elongation factor ELL (Shilatifard, A. et al., *Science* 271:1873–1876 (1996)). ELL2 is the newest addition to a growing list of biochemically defined cellular proteins that are capable of regulating the activity of the RNA polymerase II elongation complex. This list now includes six cellular elongation factors: SII, P-TEFb, TFIIF, Elongin (SIII), ELL, and ELL2, which fall into two distinct functional classes (Reines, D. et al., *Trends. Biochem. Sci.* 21:351–355 (1996)).

SII and P-TEFb were shown previously to prevent RNA polymerase II from arresting transcription prematurely. SII protects RNA polymerase II from arrest at a variety of transcriptional impediments, including specific DNA sequences that act as intrinsic arrest sites and some DNA bound proteins and drugs. SII promotes passage of RNA polymerase II through these transcriptional impediments by a mechanisms involving reiterative endonucleolytic cleavage and re-extension of nascent transcripts held in the polymerase site (Reines, D., in *Transcription: Mechanisms and Regulations*, eds. Conaway, R. C. & Conaway, J. W. (Raven Press, New York) (1994), pp. 263–278). P-TEFb promotes passage of RNA polymerase II through DRB-sensitive arrest sites within a few hundred nucleotides of promoters, by a mechanism that may involve phosphorylation of the RNA polymerase II CTD (Marshall, N. F. & Price, D. H., *J. Biol. Chem.* 270:12335–12338 (1995), Marshall, N. F. et al., *J. Biol. Chem.* 271:27176–27183 (1996)). TFIIF, Elongin (SIII), and ELL were all shown previously to increase the overall rate of elongation by RNA polymerase II by decreasing the frequency or duration of transient pausing by the enzyme at many sites along DNA templates (Shilatifard, A. et al., *Science* 271:1873–1876 (1996), Price, D. H. et al., *Mol. Cell. Biol.* 9:1465–1475 (1989), Aso, T. et al., *Science* 269:1439–1443 (1995)). Neither TFIIF, Elongin (SIII), nor ELL is capable of releasing RNA polymerase II from SII- or DRB-sensitive arrest sites.

As we have shown here, ELL2 regulates the activity of the RNA polymerase II elongation complex by a mechanism more closely resembling those of TFIIF, Elongin (SIII), and ELL. ELL2 appears to increase the overall rate of elongation by RNA polymerase II during both promoter-dependent and independent transcription. In contrast to SII, ELL2 does not release RNA polymerase II from arrest or promote the nascent transcription cleavage reaction.

Although ELL2 and ELL are related proteins, they do not share sequence similarity throughout their entire ORFs. Alignment of their ORFs revealed that ELL2 and ELL share three regions of high homology: an N-terminal region between ELL2 residues 7 and 353, a short lysine-rich region between ELL2 residues 443–474, and a C-terminal region between ELL2 residues 516–640. Structure-function analysis reveals that ELL2 transcriptional activity resides in conserved region 1 in the ELL2 N-terminus. Neither the conserved lysine-rich region 2 nor the conserved C-terminal region 3 is required for ELL2 transcriptional activity. The functions of regions 2 and 3 are presently unknown.

A homology search of the GenBank database revealed that conserved region 3 of ELL2 and ELL bears a striking resemblance to the ZO-1 binding domain of occludin (Furuse, M. et al., *J. Cell. Bio.* 127:1617–1626 (1994)), an integral membrane protein localized at tight junctions in mammalian cells (Furuse, M. et al., *J. Cell. Bio.* 123:1777–1788 (1993)). ZO-1 is a member of the family of membrane-associated guanylate kinase homologs (MAGUKs) believed to be important in signal transduction originating from sites of cell-cell contact (Willott, E. et al., *Proc. Natl. Acad. Sci. U.S.A.* 90:7834–7838 (1993)). The founding member of the MAGUK family of putative signaling proteins is the product of the lethal(1)discs large-1 (dlg) tumor suppressor gene of Drosophila (Woods, D. F. & Bryant, P. J., *Cell* 66:541–464(1994)). Other members of the MAGUK family include ZO-2, a second tight junction protein (Jesaitis, L. A. & Goodenough, D. A., *J. Cell. Biol.* 124:949–961(1994)), PSD-95/SAP-90, which localizes to synaptic junctions (Kistner, U. et al., *J. Biol. Chem.* 268:4580–4583 (1993)), p55, which participates in erythrocyte membrane-cytoskeletal interactions (Ruff, P. et al., *Proc. Natl. Acad. Sci. U.S.A.* 88:6595–6599(1991)), and hdlg, a human homolog of Drosophila dig (Lue, R. A. et al., *Proc. Natl. Acad. Sci. U.S.A.* 91:9818–9822 (1994)). Recently, ZO-1, which is found exclusively in the cytosol of contact-inhibited cultured cells, was found to translocate to the nucleus in subconfluent cells, suggesting that ZO-1 is involved in signaling pathways controlled by cell-cell contact (Kistner, U. et al., *J. Biol. Chem.* 268:4580–4583 (1993)). Intriguingly, the intracellular localization of the product of the von Hippel-Lindau tumor suppressor gene, which has been shown to interact with and negatively regulate the B and C regulatory subunits of Elongin, is similarly regulated by cell density (Lee, S. et al., *Proc. Natl. Acad. Sci. U.S.A.* 93:1770–1775 (1996)). Whether conserved region 3 of ELL2 or ELL is capable of interacting with ZO-1 is presently unknown. However, ELL2 and ELL could be regulated via a signal transduction pathway involving ZO-1 or ZO-1-like protein(s).

Finally, because of their abilities to stimulate elongation by RNA polymerase II through a wide variety of DNA template sequences, TFIIF, Elongin (SIII), and ELL have been considered "general" transcription factors. Our finding that the ELL2 and ELL genes are expressed in many of the same tissues, but that the ratio of ELL2 and ELL mRNAs exhibits tissue to tissue variation, raises the possibility that ELL2 and ELL may perform gene- or tissue-specific functions.

What is claimed is:

1. An isolated protein comprising an amino acid sequence at least 90% identical to amino acids 51 to 640 of SEQ ID NO:2, wherein said protein has the activity of increasing the overall rate of elongation by RNA polymerase II during transcription.

2. The protein of claim 1, comprising an amino acid sequence at least 95% identical to amino acids 51 to 640 of SEQ ID NO:2.

3. The protein of claim 1, comprising an amino acid sequence at least 90% identical to amino acids 11 to 640 of SEQ ID NO:2.

4. The protein of claim 3, comprising an amino acid sequence at least 95% identical to amino acids 11 to 640 of SEQ ID NO:2.

5. The protein of claim 3, comprising an amino acid sequence at least 90% identical to amino acids 1 to 640 of SEQ ID NO:2.

6. The protein of claim 5, comprising an amino acid sequence at least 95% identical to amino acids 1 to 640 of SEQ ID NO:2.

7. The protein of claim 1, which is produced by a recombinant host cell.

8. The protein of claim 1, which comprises a heterologous polypeptide.

9. A composition comprising the protein of claim 1 and a carrier.

10. A method for producing the protein of claim 1, comprising:

(a) culturing a host cell under conditions suitable to produce the protein; and (b) recovering the protein from the cell culture.

11. An isolated protein produced by a method comprising:

(a) expressing the protein of claim 1 in a cell; and (b) recovering said protein.

12. An isolated protein comprising an amino acid sequence at least 90% identical to amino acids 1 to 498 of SEQ ID NO:2, wherein said protein has the activity of increasing the overall rate of elongation by RNA polymerase II during transcription.

13. The protein of claim 12, comprising an amino acid sequence at least 95% identical to amino acids 1 to 498 of SEQ ID NO:2.

14. The protein of claim 12, which is produced by a recombinant host cell.

15. The protein of claim 12, which comprises a heterologous polypeptide.

16. A composition comprising the protein of claim 12 and a carrier.

17. A method for producing the protein of claim 12, comprising:

(a) culturing a host cell under conditions suitable to produce the protein; and (b) recovering said protein from the cell culture.

18. An isolated protein produced by a method comprising:

(a) expressing the protein of claim 12 in a cell; and (b) recovering said protein.

19. An isolated protein comprising an amino acid sequence at least 90% identical to amino acids 1 to 388 of SEQ ID NO:2, wherein said protein has the activity of increasing the overall rate of elongation by RNA polymerase II during transcription.

20. The protein of claim 19, comprising an amino acid sequence at least 95% identical to amino acids 1 to 388 of SEQ ID NO:2.

21. The protein of claim 19, which is produced by a recombinant host cell.

22. The protein of claim 19, which comprises a heterologous polypeptide.

23. A composition comprising the protein of claim 19 and a carrier.

24. A method for producing the protein of claim 19, comprising:

(a) culturing a host cell under conditions suitable to produce the protein; and (b) recovering said protein from the cell culture.

25. An isolated protein produced by a method comprising:

a) expressing the protein of claim 19 in a cell; and b) recovering said protein.

26. An isolated protein comprising an amino acid sequence at least 90% identical to the amino acid sequence encoded by the cDNA in ATCC Deposit No. 97863, wherein said protein has the activity of increasing the overall rate of elongation by RNA polymerase II during transcription.

27. The protein of claim 26, comprising an amino acid sequence at least 95% identical to the amino acid sequence encoded by the cDNA in ATCC Deposit No. 97863.

28. The protein of claim 26, which is produced by a recombinant host cell.

29. The protein of claim 26, which comprises a heterologous polypeptide.

30. A composition comprising the protein of claim 26 and a carrier.

31. A method for producing the protein of claim 25, comprising:

(a) culturing a host cell under conditions suitable to produce the protein; and (b) recovering said protein from the cell culture.

32. An isolated protein produced by a method comprising:

(a) expressing the protein of claim 26 in a cell; and (b) recovering said protein.

33. An isolated protein comprising amino acids 51 to 640 of SEQ ID NO:2, wherein said protein has the activity of increasing the overall rate of elongation by RNA polymerase II during transcription.

34. The protein of claim 33, comprising amino acids 11 to 640 of SEQ ID NO:2.

35. The protein of claim 34, comprising amino acids 1 to 640 of SEQ ID NO:2.

36. The protein of claim 33, which is produced by a recombinant host cell.

37. The protein of claim 33, which comprises a heterologous polypeptide.

38. A composition comprising the protein of claim 33 and a carrier.

39. A method for producing the protein of claim 33, comprising:

(a) culturing a host cell under conditions suitable to produce the protein; and (b) recovering said protein from the cell culture.

40. An isolated protein produced by a method comprising:

(a) expressing the protein of claim 33 in a cell; and (b) recovering said protein.

41. An isolated protein comprising amino acids 1 to 498 of SEQ ID NO:2, wherein said protein has the activity of increasing the overall rate of elongation by RNA polymerase II during transcription.

42. The protein of claim 41, which is produced by a recombinant host cell.

43. The protein of claim 41, which comprises a heterologous polypeptide.

44. A composition comprising the protein of claim 41 and a carrier.

45. A method for producing the protein of claim 41, comprising:

(a) culturing a host cell under conditions suitable to produce the protein; and (b) recovering said protein from the cell culture.

46. An isolated protein produced by a method comprising:

(a) expressing the protein of claim 41 in a cell; and (b) recovering said protein.

47. An isolated protein comprising amino acids 1 to 388 of SEQ ID NO:2, wherein said protein has the activity of increasing the overall rate of elongation by RNA polymerase II during transcription.

48. The protein of claim 47, which is produced by a recombinant host cell.

49. The protein of claim 47, which comprises a heterologous polypeptide.

50. A composition comprising the protein of claim 47 and a carrier.

51. A method for producing the protein of claim 47, comprising:

(a) culturing a host cell under conditions suitable to produce the protein; and (b) recovering said protein from the cell culture.

52. An isolated protein produced by a method comprising:

(a) expressing the protein of claim 47 in a cell; and (b) recovering said protein.

53. An isolated protein comprising the complete amino acid sequence encoded by the cDNA in ATCC Deposit No. 97863.

54. The protein of claim 53, which is produced by a recombinant host cell.

55. The protein of claim 53, which comprises a heterologous polypeptide.

56. A composition comprising the protein of claim 53 and a carrier.

57. A method for producing the protein of claim 53, comprising:

(a) culturing a host cell under conditions suitable to produce the protein; and (b) recovering said protein from the cell culture.

58. An isolated protein produced by a method comprising:

(a) expressing the protein of claim 53 in a cell; and (b) recovering said protein.

* * * * *

UNITED STATES PATENT AND TRADEMARK OFFICE

CERTIFICATE OF CORRECTION

PATENT NO. : 6,379,923 B1
DATED : April 30, 2002
INVENTOR(S) : Duan et al.

It is certified that error appears in the above-identified patent and that said Letters Patent is hereby corrected as shown below:

Column 58,
Line 63, please delete "claim 25" and insert therein -- claim 26 --.

Signed and Sealed this

Twenty-fourth Day of September, 2002

*Attest:*

JAMES E. ROGAN

*Attesting Officer*

*Director of the United States Patent and Trademark Office*